US008269029B2

(12) United States Patent  
Masel et al.

(10) Patent No.: US 8,269,029 B2
(45) Date of Patent: Sep. 18, 2012

(54) WATER REPELLENT METAL-ORGANIC FRAMEWORKS, PROCESS FOR MAKING AND USES REGARDING SAME

(75) Inventors: Richard I Masel, Campaign, IL (US); Zheng Ni, Champaign, IL (US); Qingmei Chen, Savory, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 645 days.

(21) Appl. No.: 12/420,588

(22) Filed: Apr. 8, 2009

(65) Prior Publication Data

US 2010/0075123 A1 Mar. 25, 2010

Related U.S. Application Data

(60) Provisional application No. 61/043,288, filed on Apr. 8, 2008.

(51) Int. Cl.
*C07F 15/00* (2006.01)

(52) U.S. Cl. ............ 556/132; 556/1; 556/115; 556/136; 556/142; 534/15

(58) Field of Classification Search ............... 534/15; 556/1, 115, 132, 136, 142
See application file for complete search history.

(56) References Cited

U.S. PATENT DOCUMENTS

| | | |
|---|---|---|
| 2,901,623 A | 8/1959 | Wouters |
| 3,149,941 A | 9/1964 | Barnitz et al. |
| 3,168,823 A | 2/1965 | Reinecke et al. |
| 3,345,858 A | 10/1967 | Fenske |
| 3,357,232 A | 12/1967 | Lauer |
| 3,461,519 A | 8/1969 | Raschle |
| 3,538,744 A | 11/1970 | Karasek |
| 3,568,411 A | 3/1971 | Dravnicks et al. |
| 3,585,863 A | 6/1971 | Hrdina |
| 3,675,466 A | 7/1972 | Linenberg |
| 3,733,908 A | 5/1973 | Linenberg |
| 3,769,837 A | 11/1973 | Kraus |
| 3,797,318 A | 3/1974 | Palm |
| 3,807,217 A | 4/1974 | Wilkins et al. |
| 3,897,679 A | 8/1975 | Guild |
| 3,923,461 A | 12/1975 | Barden |
| 3,925,022 A | 12/1975 | Showalter et al. |
| 3,950,980 A | 4/1976 | Braun et al. |
| 3,985,017 A | 10/1976 | Goldsmith |
| 4,040,085 A | 8/1977 | Jouanny |
| 4,040,805 A | 8/1977 | Nelms et al. |
| 4,084,440 A | 4/1978 | Carpenter et al. |
| 4,128,008 A | 12/1978 | Linenberg |

(Continued)

OTHER PUBLICATIONS

International Search Report, International Preliminary Report on Patentability and the Written Opinion, corresponding to the PCT application PCT/US06/29296 filed Jul. 26, 2006.

(Continued)

*Primary Examiner* — Porfirio Nazario Gonzalez
(74) *Attorney, Agent, or Firm* — Kilpatrick Townsend & Stockton LLP

(57) ABSTRACT

Microwave assisted synthesis may be used to produce water-repellent metallic organic frameworks (MOFs) molecules. The water-repellent MOFs contain non-polar functional groups, such as a trifluoromethoxy group, which has a strong water repellent effect. The water-repellent MOF, when exposed to water vapor for one week does not result in a significant X-ray power pattern change. The water-repellent MOFs may be suitable as an adsorbent in many industrial applications, such as gas chromatography.

20 Claims, 8 Drawing Sheets

U.S. PATENT DOCUMENTS

| | | | |
|---|---|---|---|
| 4,129,424 A | 12/1978 | Armond | |
| 4,180,389 A | 12/1979 | Paul | |
| 4,235,097 A | 11/1980 | Kring et al. | |
| 4,293,316 A | 10/1981 | Block | |
| 4,293,415 A | 10/1981 | Bente et al. | |
| 4,301,114 A | 11/1981 | Rounbehler et al. | |
| 4,376,641 A | 3/1983 | Nestrick et al. | |
| 4,399,688 A | 8/1983 | Dennis | |
| 4,451,816 A | 5/1984 | Ball | |
| 4,498,850 A | 2/1985 | Perlov et al. | |
| 4,509,964 A | 4/1985 | Hubball et al. | |
| 4,541,268 A | 9/1985 | Odernheimer | |
| 4,585,209 A | 4/1986 | Aine et al. | |
| 4,599,095 A | 7/1986 | Barnes et al. | |
| 4,628,576 A | 12/1986 | Giachino et al. | |
| 4,647,013 A | 3/1987 | Giachino et al. | |
| 4,698,071 A | 10/1987 | Elias | |
| 4,701,306 A | 10/1987 | Lawrence et al. | |
| 4,713,091 A | 12/1987 | Govind | |
| 4,735,691 A | 4/1988 | Green et al. | |
| 4,759,210 A | 7/1988 | Wohltjen | |
| 4,778,666 A | 10/1988 | Chu et al. | |
| 4,805,441 A | 2/1989 | Sides et al. | |
| 4,819,477 A | 4/1989 | Fisher et al. | |
| 4,821,999 A | 4/1989 | Ohtaka | |
| 4,826,131 A | 5/1989 | Mikkor | |
| 4,865,746 A | 9/1989 | Overfield | |
| 4,885,830 A | 12/1989 | Ohtaka | |
| 4,895,500 A | 1/1990 | Hok | |
| 4,915,051 A | 4/1990 | Martinek | |
| 4,915,843 A | 4/1990 | Taniguchi et al. | |
| 4,977,095 A | 12/1990 | Zaromb | |
| 4,997,676 A | 3/1991 | Lefebvre | |
| 5,014,541 A | 5/1991 | Sides et al. | |
| 5,055,346 A | 10/1991 | Rohrbacher | |
| 5,069,419 A | 12/1991 | Jerman | |
| 5,082,242 A | 1/1992 | Bonne et al. | |
| 5,083,019 A | 1/1992 | Spangler | |
| 5,092,155 A | 3/1992 | Rounbehler et al. | |
| 5,092,217 A | 3/1992 | Achter et al. | |
| 5,092,218 A | 3/1992 | Fine et al. | |
| 5,110,551 A | 5/1992 | Michal | |
| 5,123,276 A | 6/1992 | Hartman et al. | |
| 5,142,143 A | 8/1992 | Fite et al. | |
| 5,162,652 A | 11/1992 | Cohen et al. | |
| 5,173,264 A | 12/1992 | Zaromb et al. | |
| 5,176,358 A | 1/1993 | Bonne et al. | |
| 5,180,623 A | 1/1993 | Ohnstein | |
| 5,216,273 A | 6/1993 | Doering et al. | |
| 5,224,972 A | 7/1993 | Frye et al. | |
| 5,288,310 A | 2/1994 | Peters et al. | |
| 5,294,418 A | 3/1994 | Ramprasad et al. | |
| 5,322,258 A | 6/1994 | Bosch et al. | |
| 5,323,999 A | 6/1994 | Bonne et al. | |
| 5,328,851 A | 7/1994 | Zaromb | |
| 5,395,589 A | 3/1995 | Nacson | |
| 5,417,235 A | 5/1995 | Wise et al. | |
| 5,441,597 A | 8/1995 | Bonne et al. | |
| 5,465,607 A | 11/1995 | Corrigan et al. | |
| 5,468,851 A | 11/1995 | Seeman et al. | |
| 5,481,110 A | 1/1996 | Krishnaswamy et al. | |
| 5,482,677 A | 1/1996 | Yao et al. | |
| 5,522,918 A | 6/1996 | Shiramizu | |
| 5,532,129 A | 7/1996 | Heller | |
| 5,551,278 A | 9/1996 | Rounbehler et al. | |
| 5,585,575 A | 12/1996 | Corrigan et al. | |
| 5,589,396 A | 12/1996 | Frye et al. | |
| 5,619,177 A | 4/1997 | Johnson et al. | |
| 5,648,508 A | 7/1997 | Yaghi | |
| 5,720,798 A | 2/1998 | Nickerson et al. | |
| 5,753,832 A | 5/1998 | Bromberg et al. | |
| 5,763,360 A | 6/1998 | Gundel et al. | |
| 5,795,368 A | 8/1998 | Wright et al. | |
| 5,830,427 A | 11/1998 | Bedard et al. | |
| 5,836,750 A | 11/1998 | Cabuz | |
| 5,854,431 A | 12/1998 | Linker et al. | |
| 5,876,830 A | 3/1999 | Michl et al. | |
| 5,899,218 A | 5/1999 | Dugan | |
| 5,941,501 A | 8/1999 | Biegelsen et al. | |
| 5,970,804 A | 10/1999 | Robbat, Jr. | |
| 6,000,676 A | 12/1999 | Zengerle et al. | |
| 6,026,834 A | 2/2000 | Azima | |
| 6,085,601 A | 7/2000 | Linker et al. | |
| 6,098,661 A | 8/2000 | Yim et al. | |
| 6,110,247 A | 8/2000 | Birmingham et al. | |
| 6,126,140 A | 10/2000 | Johnson et al. | |
| 6,129,331 A | 10/2000 | Henning et al. | |
| 6,165,254 A | 12/2000 | Kawakami et al. | |
| 6,171,378 B1 | 1/2001 | Manginell et al. | |
| 6,182,941 B1 | 2/2001 | Scheurenbrand et al. | |
| 6,187,412 B1 | 2/2001 | Armacost et al. | |
| 6,215,221 B1 | 4/2001 | Cabuz et al. | |
| 6,223,584 B1 | 5/2001 | Mustacich et al. | |
| 6,251,260 B1 | 6/2001 | Heller et al. | |
| 6,345,545 B1 | 2/2002 | Linker et al. | |
| 6,355,793 B1 | 3/2002 | Lin | |
| 6,372,932 B1 | 4/2002 | Kepert et al. | |
| 6,384,253 B1 | 5/2002 | Khan | |
| 6,454,840 B1 | 9/2002 | Gellert et al. | |
| 6,455,003 B1 | 9/2002 | Anvia et al. | |
| 6,470,904 B1 | 10/2002 | Tai et al. | |
| 6,481,263 B1 | 11/2002 | Haley et al. | |
| 6,491,740 B1 | 12/2002 | Wang et al. | |
| 6,517,610 B1 | 2/2003 | de la Houssaye | |
| 6,523,393 B1 | 2/2003 | Linker et al. | |
| 6,527,835 B1 | 3/2003 | Manginell et al. | |
| 6,557,820 B2 | 5/2003 | Wetzel et al. | |
| 6,568,286 B1 | 5/2003 | Cabuz | |
| 6,604,406 B1 | 8/2003 | Linker et al. | |
| 6,607,580 B1 | 8/2003 | Hastings et al. | |
| 6,607,700 B1 | 8/2003 | Apte et al. | |
| 6,610,125 B2 | 8/2003 | Tripp et al. | |
| 6,626,416 B2 | 9/2003 | Sharma et al. | |
| 6,626,417 B2 | 9/2003 | Winger et al. | |
| 6,649,129 B1 | 11/2003 | Neal | |
| 6,656,738 B1 | 12/2003 | Vogel et al. | |
| 6,663,697 B1 | 12/2003 | Kottenstette et al. | |
| 6,666,907 B1 | 12/2003 | Manginell et al. | |
| 6,670,024 B1 | 12/2003 | Yu | |
| 6,685,841 B2 | 2/2004 | Lopez et al. | |
| 6,706,091 B1 | 3/2004 | Robinson et al. | |
| 6,719,828 B1 | 4/2004 | Lovell et al. | |
| 6,749,826 B2 | 6/2004 | Alcaraz et al. | |
| 6,759,013 B2 | 7/2004 | Kaltenbach et al. | |
| 6,772,513 B1 | 8/2004 | Frye-Mason et al. | |
| 6,773,674 B2 | 8/2004 | Bannister et al. | |
| 6,783,680 B2 | 8/2004 | Malik | |
| 6,793,753 B2 | 9/2004 | Unger et al. | |
| 6,814,781 B2 | 11/2004 | Tonkovich et al. | |
| 6,830,229 B2 | 12/2004 | Wetzel et al. | |
| 6,834,671 B2 | 12/2004 | Cotte et al. | |
| 6,837,476 B2 | 1/2005 | Cabuz et al. | |
| 6,838,640 B2 | 1/2005 | Wise et al. | |
| 6,840,120 B2 | 1/2005 | Sakairi et al. | |
| 6,848,325 B2 | 2/2005 | Parmeter et al. | |
| 6,875,257 B2 | 4/2005 | Rodgers | |
| 6,893,564 B2 | 5/2005 | Mueller et al. | |
| 6,902,701 B1 | 6/2005 | Hughes et al. | |
| 6,910,394 B2 | 6/2005 | Kriel | |
| 6,913,697 B2 | 7/2005 | Lopez et al. | |
| 6,914,220 B2 | 7/2005 | Tian et al. | |
| 6,929,679 B2 | 8/2005 | Muller et al. | |
| 6,930,193 B2 | 8/2005 | Yaghi et al. | |
| RE38,797 E | 9/2005 | Linker et al. | |
| 6,965,026 B2 | 11/2005 | Zaworotko et al. | |
| 6,967,103 B2 | 11/2005 | Schwartz et al. | |
| 6,967,193 B1 | 11/2005 | Dang et al. | |
| 6,968,862 B2 | 11/2005 | Cabuz et al. | |
| 6,978,657 B1 | 12/2005 | Baumann et al. | |
| 6,984,524 B2 | 1/2006 | Nguyen et al. | |
| 6,986,365 B2 | 1/2006 | Henning et al. | |
| 6,986,500 B2 | 1/2006 | Giousouf et al. | |
| 6,989,044 B2 | 1/2006 | Zhang et al. | |
| 6,998,040 B2 | 2/2006 | Malik et al. | |
| 7,000,452 B2 | 2/2006 | Bonne et al. | |
| 7,008,193 B2 | 3/2006 | Najafi et al. | |
| 7,014,165 B2 | 3/2006 | Ji et al. | |

| | | | |
|---|---|---|---|
| 7,052,677 | B1 | 5/2006 | Raptis et al. |
| 7,147,695 | B2 | 12/2006 | Mitra |
| 7,654,129 | B2 | 2/2010 | Bonne et al. |
| 7,695,681 | B2 | 4/2010 | Wang et al. |
| 2002/0175302 | A1 | 11/2002 | Wetzel |
| 2003/0004364 | A1 | 1/2003 | Yaghi et al. |
| 2003/0078311 | A1 | 4/2003 | Muller et al. |
| 2003/0146401 | A1 | 8/2003 | Wetzel |
| 2003/0148165 | A1 | 8/2003 | Muller et al. |
| 2003/0222023 | A1 | 12/2003 | Mueller et al. |
| 2003/0231967 | A1 | 12/2003 | Najafi et al. |
| 2003/0234376 | A1 | 12/2003 | Cabuz et al. |
| 2004/0097724 | A1 | 5/2004 | Muller et al. |
| 2004/0137300 | A1 | 7/2004 | Gemmen et al. |
| 2004/0191125 | A1 | 9/2004 | Kellogg et al. |
| 2004/0225134 | A1 | 11/2004 | Yaghi et al. |
| 2004/0249189 | A1 | 12/2004 | Mueller et al. |
| 2004/0265670 | A1 | 12/2004 | Muller et al. |
| 2005/0004404 | A1 | 1/2005 | Muller et al. |
| 2005/0067029 | A1 | 3/2005 | Henning |
| 2005/0098435 | A1 | 5/2005 | Jacobson et al. |
| 2005/0101027 | A1 | 5/2005 | Haas |
| 2005/0124819 | A1 | 6/2005 | Yaghi et al. |
| 2005/0154222 | A1 | 7/2005 | Muller et al. |
| 2005/0164870 | A1 | 7/2005 | Shan et al. |
| 2005/0192175 | A1 | 9/2005 | Yaghi et al. |
| 2006/0037477 | A1 | 2/2006 | Lopez et al. |
| 2006/0049101 | A1 | 3/2006 | Suib et al. |
| 2006/0057057 | A1 | 3/2006 | Muller et al. |
| 2006/0071192 | A1 | 4/2006 | Ohmi et al. |
| 2006/0099398 | A1 | 5/2006 | Hesse et al. |
| 2006/0113231 | A1 | 6/2006 | Malik |
| 2006/0144237 | A1 | 7/2006 | Liang et al. |
| 2006/0175238 | A1 | 8/2006 | Lautamo |
| 2006/0200044 | A1 | 9/2006 | Freeman et al. |
| 2006/0252641 | A1 | 11/2006 | Yaghi et al. |
| 2007/0023719 | A1 | 2/2007 | Shannon et al. |
| 2007/0074717 | A1 | 4/2007 | Law et al. |
| 2007/0172960 | A1 | 7/2007 | Malik et al. |
| 2009/0131643 | A1 | 5/2009 | Ni et al. |
| 2009/0178563 | A1 | 7/2009 | Masel et al. |
| 2009/0211452 | A1 | 8/2009 | Masel et al. |
| 2010/0075123 | A1 | 3/2010 | Masel et al. |
| 2010/0132547 | A1 | 6/2010 | Masel et al. |

OTHER PUBLICATIONS

International Preliminary Report on Patentability and Written Opinion corresponding to the PCT application PCT/US06/38998 filed Oct. 6, 2006.
International Search Report and Written Opinion corresponding to the PCT application PCT/US07/009243 filed Apr. 13, 2007.
International Preliminary Report and Written Opinion corresponding to the PCT application PCT/US2008/053959 filed Feb. 14, 2008.
Panda, A. B. et al., Microwave Synthesis of Highly Aligned Ultra Narrow Semiconductor Rods and Wires, J. Am. Chem. Soc., 128:2790-2791 (2006).
Tompsett, G. A. et al., Microwave Synthesis of Nanoporous Materials, ChemPhysChem, 7:296-319 (2006).
Lu, Q. et al., Biomolecule and/or Microwave-Assisted Solvothermal Syntheses of Nanomaterials, AZo Journal of Materials Online vol. 1, (2005).
Grudpan, K. et al., Flow injection spectrophotometric determination of As(III) and As(V) using molybdate reagent with solid phase extraction in-valve column, Indian Journal of Chemistry, 42A:2939-2944 (2003).
Luis Castaner et al., Speed-energy optimization of electrostatic actuators based on Pull-in, IEEE Journal of Microelectromechanical Systems, vol. 8, No. 3, pp. 257-265 (1999).
Han et al., Micro-fabricated membrane gas valves with a non-stiction coating deposited by $C_4F_8$/Ar plasma, J. Micromech. Microeng. 18 (2008) 095015, pp. 1-9.
Yeom et al., The design, fabrication and characterization of a silicon microheater for an integrated MEMS gas preconcentrator, J. Micromech. Microeng. 18 (2008) 125001, pp. 1-12.
Han et al. Surface energy approach and AFM verification of the (CF)n treated surface effect and its correlation with adhesion reduction in microvalves, J. Micromech. Microeng. 19 (2009) 085017, pp. 1-9.

Radadia et al., The fabrication of all-silicon micro gas chromatography columns using gold diffusion eutectic bonding, J. Micromech. Microeng. 20 (2010) 015002, pp. 1-7.
Radadia et al., Micromachined GC Columns for Fast Separation of Organophosphonate and Organosulfur Compounds, Anal. Chem. 2008, 80, pp. 4087-4094.
Radadia et al., Partially Buried Microcolumns for Micro Gas Analyzers, Anal. Chem. 2009, 81, pp. 3471-3477.
Han et al., Smooth Contact Capacitive Pressure Sensors in Touch- and Peeling-Mode Operation, IEEE Sensors Journal, vol. 9, No. 3, Mar. 2009, pp. 199-206.
Radadia et al., The Effect of Microcolumn Geometry on the Performance of Micro-Gas Chromatography Columns for Chip Scale Gas Analyzers, Sensors and Actuators B: Chemical (2010), doi:10.1016/j.snb.2010.07.002, pp. 1-29.
Bae et al., A Bidirectional Electrostatic Microvalve With Microsecond Switching Performance, Journal of Microelectromechanical Systems, vol. 16, No. 6, Dec. 2007, pp. 1461-1471.
Zhong et al., Characterization of a high-performance portable GC with a chemiresistor array detector, Analyst, 2009, 134, pp. 283-293.
Groves et al., Analyzing organic vapors in exhaled breath using a surface acoustic wave sensor array with preconcentration: Selection and characterization of the preconcentrator adsorbent, Analytica Chimica Acta 371 (1998) pp. 131-143.
Zheng Ni, et al., "Rapid Production of Metal-Organic Frameworks via Microwave-Assisted Solvothermal Synthesis," J. Am. Chem. Soc.
Jay W. Grate, et al., "Progressive Thermal Desorption of Vapor Mixtures from a Preconcentrator with a Porous Metal Foam Internal Architecture and Variable Thermal Ramp Rates," pp. 1867-1875.
R. W. Jotham, et al., "Anti ferromagnetism in transition-metal complexes. Part IV. Low-lying excited states of binuclear copper (II) carboxylate complexes," J. C. S. Dalton, pp. 428-438.
K. Tamada, et al., "The steady two-dimensional flow of viscous fluid at low Reynolds numbers passing through an infinite row of equal parallel circular cylinders," Quart. J. Mech. Appl. Math., 10, 1957, 425-432.
H. Hasimoto, "On the periodic fundamental solutions of the Stokes equations and their application to viscous flow past a cubic array of spheres," J. Fluid Mech., 5, 1959, pp. 317-328.
Michinobu Kato, et al., "Copper (II) complexes with subnormal magnetic moments," Richard Chemistry Lab, Tulane University, New Orleans Louisiana, Dec. 20, 1963 pp. 99-128.
Joseph B. Keller, "Viscous flow through a grating or lattice of cylinders," J. Fluid Mech. 18, 1964, 94-96.
Wolfgang Micklitz, et al., Heptadecanuclear mixed metal iron oxo-hydroxo complexes, $[Fe_{16}MO_{10}(OH)_{10}(O_2CPh)_{20}]$ M = Mn or Co, structurally comprised of two fragments derived from $[Fe_{11}O_6(OH)_6(O_2CPh)_{15}]$ Journal American Chemical Society (1989) vol. 111, pp. 6856-6858.
Bernard F. Hoskins, et al,, "Infinite polymeric frameworks consisting of three dimensionally linked rod-like segments," Journal of the American Chemical Society, vol. 111 No. 15, (1989) pp. 5962-5964.
Sergiu M. Gorun, et al., "Magnetostructural correlations in magnetically coupled (µ-Oxo)diiron(III) complexes," Inorganic Chemistry, 1991, 30(7) pp. 1625-1630.
Vinod S. Nair, et al., "Iron Oxo aggregation: $Fe_3$ to $Fe_6$. Synthesis, structure, and magnetic properties of the hexanuclear dication $[Fe_6(\mu_4-O)_2(\mu_2-OMe)_8(OMe)_4(tren)_2]^{2+}$, a soluble, crystalline model of iron Oxo hydroxo nanoparticles, the core of ferritin and rust formation," Inorganic Chemistry (1992) vol. 31, pp. 4048-4050.
Steven C. Shoner, et al., "Neutral catecholate derivatives of manganese and iron: Synthesis and characterization of the metal-oxygen cubane-like species $M_4(DBCat)_4(py)_6$(M = Mn, Fe), the trinuclear complex $Mn_3(DBCat)_4(py)_4$ and the dimers $M_2(DBCat)_2(py)_n$(M = Mn, n = 6; M = Fe, n = 4,6)," Inorganic Chemistry (1992), 31, pp. 1001-1010.
C.T. Kresge, et al., "Ordered mesoporous molecular sieves synthesized by a liquid-crystal template mechanism," Nature, vol. 359, Oct. 22, 1992, pp. 710-712.
Kingsley L. Taft, et al., "Iron and manganese alkoxide cubes," Journal of American Chemical Society, (1993) vol. 115, pp. 11753-11766.

Andreas Stein, et al., "Turning down the heat: design and mechanism in solid-state synthesis," Science, vol. 259, No. 5101, Mar. 12, 1993, pp. 1558-1564.

Alan Wilson, et al., "Detection of Nitro Compounds by Organic Semiconductor Sensors," Sensors and Actuators B 18-19, 1994, pp. 511-514.

Kingsley L. Taft, et al., "Synthesis, structure, and electronic properties of a mixed-valent dodecairon Oxo complex, a model for the biomineralization of ferritin," Inorganic Chemistry, (1994) 33, pp. 1510-1520.

B.F. Abrahams, et al., "Assembly of porphyrin building blocks into network structures with large channels," Nature vol. 369, Jun. 30, 1994 pp. 727-729.

O.M. Yaghi, et al., "Hydrothermal Synthesis of a Metal-Organic Framework Containing Large Rectangular Channels," J. Am. Chem. Soc. 1995, 117, 10401-10402.

Katerina Dimitrou, et al., "The $[CO_4O_4]^{4+}$ cubane as a quadruply-bridging unit: the mixed-valence cluster $[Co_8O_4(O_2CPh)_{12}solv_4]$ solv = DMF, MeCN, $H_2O$)," Inorganic Chemistry, 1995, 34, pp. 4160-4166.

O. M. Yaghi, et al., "Hydrothermal synthesis of a metal-organic framework containing large rectangular channels," Journal of the American Chemical Society, 1995, vol. 117, pp. 10401-10402.

O.M. Yaghi, et al., "Selective Binding and Removal of Guests in a Microporous Metal-Organic Framework," Nature, Dec. 14, 1995, vol. 378, pp. 703-706.

O.M. Yaghi, et al., "T-Shaped Molecular Building Units in the Porous Structure of Ag(4,4'-bpy)•$NO_3$," J. Am. Chem. Soc. 1996, 118, pp. 295-296.

O. M. Yaghi, et al., "Construction of porous solids from hydrogen-bonded metal complexes of 1,3,5-benzenetricarboxylic acid," Journal of the American Chemical Society, (1996), vol. 118, pp. 9096-9101.

William A. Groves, et al., "Prototype Instrument Employing a Microsensor Array for the Analysis of Organic Vapors in Exhaled Breath," American Industrial Hygiene Association Journal 57:1103-1108, Dec. 1996.

Scott Hynek, et al., "Hydrogen storage by carbon sorption," Int. J. Hydrogen Energy vol. 22, No. 6, pp. 601-610 (1997).

Jian Lu, et al., "Coordination Polymers of Co(NCS)$_2$ with Pyrazine and 4,4'-Bipyridine: Syntheses and Stuctures," Inorganic Chemist (1997) vol. 36, pp. 923-929.

Christoph Janiak, "Functional organic analogues of zeolites bases on metal-organic coordination frameworks," Angew. Chem. Int. Ed. Engl. (1997) 36, No. 13/14 pp. 1431-1434.

Mario V. Capparelli, et al., "X-ray crystallographic structure of $Ga_8(pz)_{12}O_4Cl_4$•2thf: a novel gallium pyrazololate complex with a $Ga_4O_4$ core," Chem. Comm., (1997) pp. 937-938.

O. M. Yaghi, et al., "Crystal growth of extended solids by nonaqueous gel diffusion," Chemical Materials, (1997) vol. 9, pp. 1074-1076.

Omar M. Yaghi, et al., "Construction of a new open-framework solid from 1,3,5-cyclohexane-tricarboxylate and zinc(II) building blocks," Journal Chem. Soc. Dalton Trans., (1997), pp. 2383-2384.

Victoria A. Russell, et al,, "Nanoporous molecular sandwiches: pillared two-dimensional hydrogen-bonded networks with adjustable porosity," Science, vol. 276, Apr. 25, 1997, pp. 575-579.

Helmut Beinert, et al., "Iron-sulfur clusters: Nature's modular, multipurpose structures," Science, vol. 277, Aug. 1997, pp. 653-659.

Omar M. Yaghi, et al., "Synthetic Strategies, Structure Patterns, and Emerging properties in the chemistry of modular porous solids," Accounts of Chemical Research, vol. 31, No. 8, 1998, pp. 474-484.

William A. Groves, et al., "Analyzing organic vapors in exhaled breath using a surface acoustic wave sensor array with preconcentration: Selection and characterization of the preconcentrator adsorbent," Analytica Chimica Acta 371, 1998, pp. 131-143.

Michael W. Willer, et al., "Ligand Substitution Reactions of $[Re_6S_8Br_6]^{4-}$: A Basis Set of $Re_6S_8$ Clusters for Building Multicluster Assemblies," Inorganic Chemistry, (1998) vol. 37, pp. 328-333.

Hailian Li, et al., "Coordinatively unsaturated metal centers in the extended porous framework of $Zn_3(BDC)_3$•$6CH_3OH$ (BDC = 1,4-benzenedicarboxylate)," Journal of American Chemical Society, 1998, vol. 120, pp. 2186-2187.

Stuart L. James, et al., "Anion-templated formation of a unique inorganic 'super adamantoid' cage $[Ag_6(triphos)_4(O_3SCF_3)_4]^{2+}$ [triphos = (PPh$_2$CH$_2$)$_3$CMe]," Chemical Communication (1998) pp. 2323-2324.

M. John Plater, et al., "Hydrothermal synthesis and characterization of M(pdc)•$3H_2O$ (pdc = 2,5-pyridinedicarboxylate); M=Co, Ni, $Co_xNi_y$, (x = 0.4-0.6, y=0.6-0.4)," Journal of Chemical Research, (1998), pp. 3356-3376.

Cameron J. Kepert, et al., "A porous chiral framework of coordinated 1,3,5-benzenetricarboxylate: quadruple interpenetration of the (10,3)-a network," Chem Communication (1998) pp. 31-32.

Christopher W. Jones, et al., "Organic-functionalized molecular sieves as shape-selective catalysts," Nature vol. 393, May 7, 1998, . 52-54.

Lin, et al., "A Novel Ocupolar Metal-Organic NLO Material Based on a Chiral 2D Coordination Network," J. Am Chem. Soc. 1999, 121, 11249-11250.

Chui, et al., "A Chemically Functionalizable Nanoporous Material $[Cu_3(TMA)_2(H_2O)_3]n$," Science, 1999, vol. 283, pp. 1148-1150.

Jack Y. Lu, et al., "A new type of Two-Dimensional Metal Coordination Systems: Hydrothermal Synthesis and Properties of the First Oxalate-bpy Mixed-Ligand Framework $^2[(M (ox)(bpy)]$ (M=Fe(II), CO(II), Ni(II), Zn(II); ox = $C_2O_4^{2-}$; bpy = 4,4'-bipyridine)," Inorganic Chem. 1999, 38, pp. 2695-2704.

Srinivasan Natarajan, et al., "Layered Tin (II) Oxalates possessing large apertures," Chemical Material, 1999, 11 pp. 1633-1639.

Mitsuru Kondo, et al., "Rational synthesis of stable channel-like cavities with methane gas adsorption properties: $[\{Cu_2(pzdc)_2(L)\}_n]$ (pzdc = pyrazine-2,3-dicarboxylate; L = a pillar ligand)," Angew. Chem. Int. Ed. (1999) 38, No. ½, pp. 140-143.

Raphael G. Paptis, et al., "A $Fe^{III}$/Oxo cubane contained in an octanuclear complex of T symmetry that is stable over., five oxidation states," Angew, Chem. Int. Ed. (1999), vol. 38, No. 11, pp. 1632-1634.

Mohamed Eddaoudi, et al., "Design and synthesis of metal-carboxylate frameworks with permanent microporosity," Topics in Catalysis, 1999, vol. 9, pp. 105-111.

Stephen S.-Y Chui, et al., "A chemically functionalizable nanoporous material $[Cu_3(TMA)_2(H_2O)_3]_n$," Science, vol. 283, Feb. 19, 1999, pp. 1148-1150.

Hailian Li, et al., "Design and synthesis of an exceptionally stable and highly porous metal-organic framework," Nature, vol. 402, Nov. 18, 1999, pp. 276-279.

Seo, et al., "A Homochiral Metal-organic Porous Material for Enantioselective Separation and Catalysis," Nature, 2000, 404, pp. 982-986.

Jeongim Park, et al., "Temperature and Humidity Compensation in the Determination of Solvent Vapors with a Microsensor System," The Royal Society of Chemistry, Analyst, 2000, 125, pp. 1775-1782.

Edward T. Zellers, et al., "Evaluating Porous-Layer Open-Tubular Capillaries as Vapor Preconcentrators in a Microanalytical System," Sensors and Actuators B 67, 2000, pp. 244-253.

Qing-Yun Cai, et al., "Vapor Recognition with an Integrated Array of Polymer-Coated Flexural Plate Wave Sensors," Sensors and Actuators B 62, 2000, pp. 121-130.

M.O. O'Keeffe, et al., "Frameworks for extended solids: geometrical design principles," Journal of Solid State Chemistry 152, pp. 3-20, 2000.

Shouheng Sun, et al., "Monodisperse FePt nanoparticles and ferromagnetic FePt nanocrystals superlattices," Science. vol. 287, Mar. 17, 2000, pp. 1989-1992.

Xi Xiang Zhang, et al., "Cooperative magnetic behavior in the coordination polymers $[Cu_3(TMA)_2L_3]$ (L=$H_2O$, pyridine)," Journal of Applied Physics, vol. 87, No. 9 May 1, 2000, pp. 6007-6009.

R. Murugavel, et al., "Extended metal-organic solids based on benzenepolycarboxylic and aminobenzoic acids," Proc. Indian Acad. Sci. (Chem. Sci.) vol. 112, No. 3, Jun. 2000, pp. 273-290.

Jaheon Kim, et al., "Assembly of Metal-Organic Frameworks from Large Organic and Inorganic Secondary Building Units: New Examples and Simplifying Principles for Complex Structures," J. Am. Chem. Soc. 2001, 123, pp. 8239-8247.

Banglin Chen, et al., "Interwoven Metal-Organic Framework on a Periodic Minimal Surface with Extra-Large Pores," Science, Feb. 9, 2001, vol. 291, pp. 1021-1023.

Usan A. Bourne, et al., "Coexisting Covalent and Noncovalent Nets: Parallel Interpenetration of a Puckered Rectangular Coordination Polymer and Aromatic Noncovalent Nets," Chcm. Comm., 2001, pp. 861-862.

Chang-Ge Zheng, et al., "A novel two-dimensional layer network composed of cadmium and bridging isophthalate ligand," Inorganic Chemistry Communications 4, (2001), pp. 165-167.

Brian Moulton, et al., "From molecules to crystal engineering: supramolecular isomerism and polymorphism in network solids," Chemical Reviews, 2001, vol. 101 No. 6, pp. 1629-1658.

Cynthia Stowell, et al., "Self-Assembled honeycomb networks of gold nanocrystals," Nanoletters, (2001) vol. 1, No. 11, pp. 595-600.

Yucang Liang, et al., "Hydrothermal synthesis and characterization of the coordination polymer $[Zn(bbdc)(H_2O)]_n$ (bbdc = 4,4'-bibenzene-dicarboxylate) possessing a 3D network structure," Inorganic Chemistry Communications 4 (2001) pp. 599-601.

Yen-Hsiang Liu, et al., "Hydrothermal synthesis, crystal structure, and magnetic property of copper (II) coordination networks with chessboard tunnels," Journal of Solid State Chemist 158 2001 vol. 158, pp. 315-319.

Chuan-De Wu, et al., "Hydrothermal synthesis of two new zinc coordination polymers with mixed ligands," Inorganic Chemistry Communications 4 (2001) pp. 561-564.

H. Tamura, et al., "Semiconductor ferromagnetism in quantum dot array," Physical Stat. Sol. (b) 224, No. 3, (2001), pp. 723-725.

Ashleigh J. Fletcher, et al., "Adsorption dynamics of gases and vapors on the nanoporous metal organic framework material $Ni_2(4,4'-bipyridine)_3(NO_3)_4$: Guest modification of host sorption behavior," Journal of the American Chemical Society (2001), vol. 123, pp. 10001-10011.

Kumar Biradha, et al., "2D and 1D coordination polymers with the ability for inclusion of guest molecules: nitrobenzene, benzene, alkoxysilanes," Journal of Inclusion Phenomena and Macrocyclic Chemistry 49, (2001) pp. 201-208.

Mohamed Eddaoudi, et al., "Modular Chemistry: Secondary building units as a basis for the design of highly porous and robust metal-organic carboxylate frameworks," Acc. Chem. Res. 2001, vol. 34, pp. 319-330.

Jaheon Kim, et al., "Assembly of metal-organic frameworks from large organic and inorganic secondary building units:. new examples and simplifying principles for complex stntctures," Journal of the American Chemical Society, (2001), vol. 123, pp. 8239-8247.

Susan A. Bourne, et al., "Self-assembly of nanometer-scale secondary building units into an undulating two-dimensional network with two types of hydrophobic cavity," Angew. Chem. Int. Ed., (2001), vol. 40, No. 11, pp. 2111-2113.

Jianjiang Lu, et al., "Polygons and faceted polyhedra and nanoporous networks," Angew. Chem. Int. Ed., (2001), vol. 40, No. 11, pp. 2113-2116.

Brian Moulton, et al., "Nanoballs: nanoscale faceted polyhedra with large windows and cavities," Chem. Commun., (2001), pp. 863-864.

Heba Abourahma, et al., "Hydroxylated nanoballs: synthesis, crystal structure, solubility and crystallization on surfaces," Chem. Comm., (2001), pp. 2380-2381.

Susan A. Bourne, et al., "1-D coordination polymers containing benzenedicarboxylate," Crystal Engineering, (2001), vol. 4, pp. 25-36.

Chia-Jung Lu, et al., "A Dual-Adsorbent Preconcentrator for a Portable Indoor-VOC Microsensor System," Analytical Chemistry, vol. 73, No. 14, Jul. 15, 2001, pp. 3349-3457.

Kosal, M.E., et al., "A functional zeolite analogue assembled from metalloporphyrins," Nature Materials, 2002, vol. 1, pp. 118-121.

Xingling Xu, et al., "A nanoporous metal-organic framework based on bulky phosphane ligands," Angew. Chem. Int. Ed, (2002) 41, No. 5 pp. 764-767.

Filipe A. Almeida Paz, et al., "Synthesis and characterization of a novel modular cadmium-organic framework with biphenyl-4,4'-dicarboxylate," Eur. J. Inorg, Chem. (2002) pp. 2823-2828.

Zi-Guang Sun, et al., "Guest controlled coordination framework: syntheses, crystal structures and thermal properties of two three-dimensional structures of $[Ce_2(adipate)_3(OH_2)_4] \cdot 6H_2O$ and $[Ce_2(adipate)_3(OH_2)_4] \cdot 4H_2O \cdot$ (adipic acid)," Inorganic Chemist Communications 5 (2002) pp. 629-632.

Ljiubov Morris, et al., "Simple system for part-per-billion-level volatile organic compound analysis in groundwater and urban air," Measurement Science and Technology, 13, (2002) pp. 603-612.

Ming Wen, et al., "Porous silver (I) organometallic coordination polymer of triptycene, and the guest desorption and absorption," Inorganica Chimica Acta 340 (2002) pp. 8-14.

Edmund J. Cussen, et al., "Flexible sorption and transformation behavior in a microporous metal-organic framework," Journal of the American Chemical Society (2002), vol. 124, pp. 9574-9581.

Yu-Cang Liang, et al., "Hydrothermal syntheses, structural characterizations and magnetic properties of cobalt (II) and manganese(II) coordination polymeric complexes containing pyrazinecarboxylate ligand," Inorganica Chimica Acta 328, (2002), pp. 152-158.

Jun Tao, et al., "Assembly of a microporous metal-organic framework [Zn(bpdc)(DMSO)] (bpdc = 4,4-biphenyldicarboxylate) based on paddle-wheel units affording guest inclusion," Inorganic Chemistry Communications, (2002), vol. 5, pp. 975-977.

Mohamed Eddaoudi, et al., "Systematic Design of Pore Size and Functionality in Isoreticular MOFs and Their Application in Methane Storage," Science, Jan. 18, 2002, vol. 295, pp. 469-472.

Yaghi, et al., "Reticular Synthesis and the Design of New Materials," Nature 423, 2003, pp. 705-714.

Smithenry, D.W., et al., "A Robust Microporous Zinc Porphyrin Framework Solid," Inorg. Chem. 2003, vol. 42, pp. 7719-7721.

Jinxi Chen, et al., "A new open metal-organic framework $[(Zn_8(GeO_4)(C_8H_4O_4)_6)_n$, Constucted by Herometallic Cluster $Zn_8(GeO_4)$ Secondary Building Units," Chemist Letters vol. 32, No. 5 (2003).

Enrique Colacio, et al., "Hydrothermal syntheses, crystal structures, and properties of two- dimensional homo- and heterometallic cyanide-bridged complexes: $[CU_2(CN)_2(bpym)]$ and $[Fe((bipy)_2(CN)_4CU_2]$ [(bpym = 2,2'—Bipyrimidine, bipy = 2,2'-Bipyridine)," Inorganic Chemist 2003, 42, pp. 4209-4214.

Li-Ping Zhang, et al., "Hydrothermal synthesis and crystal structures of three novel lanthanide coordination polymers with glutarate and 1,10 phenanthroline," Journal of Molecular Structure 646 (2003) pp. 169-178.

Li-Ping Zhang, et al., "Hydrothermal synthesis and crystal structure of neodymium(III) coordination polymers with isophthalic acid and 1,10-phenanthroline," Polyhedron 22 (2003) pp. 981-987.

Hidekazu Arii, et al., "Unique three-dimensionally expanded nanoporous structure constructed with a Cu(I) and cis,cis-1,3,5-triaminocyclohexane having a 3-fold axial symmetry," Chemist Letters vol. 32 No. 1 (2003) pp. 106-107.

Aleksey Vishnyakov, et al., "Nanopore structure and sorption properties of Cu-BTC metal-organic framework," Nano Letters, vol. 3, No. 6, (2003) pp. 713-718.

T. J. Prior, et al., "Designed layer assembly: a three-dimensional framework with 74% extra-framework volume by connection of infinite two-dimensional sheets," Chem. Commun., (2003), pp. 500-501.

Yang-Guang Li, et al., A novel three-dimensional metal-organic framework constructed from two-dimensional interpenetrating layers based on trinuclear cobalt clusters: $[Co_3(btec)(C_2O_4)(H_2O_2]_n$. Eur. Journal of Inorganic Chemistry (2003) pp. 2567-2571.

Sujit K. Ghosh, et al., "Coexistence of water dimer and hexamer clusters in 3D metal-organic framework structures of Ce(III) and Pr(III) with pyridine-2 6-dicarboxylic acid," Inorganic Chemistry, (2003) vol. 42, pp. 8250-8254.

Hee K. Chae, et al., "Design of frameworks with mixed triangular and octahedral building blocks exemplified by the structure of $[Zn_4O(TCA)_2]$ having the pyrite topology," Angew. Chem. Int. Ed., (2003), vol. 42, pp. 3907-3909.

Nathaniel L. Rosi, et al., "Hydrogen Storage in Microporous Metal-Organic Frameworks," Science, May 16, 2003, vol. 300, pp. 1127-1129.

Wei-Cheng Tian, et al., "Microfabricated Preconcentrator-Focuser for a Microscale Gas Chromatograph," Journal of Microelectromechanical Systems, vol. 12, No. 3, Jun. 2003, pp. 264-272.

Yun-Qi Tian, et al., "{[In₃(pzdc)₆]³⁻} Metal-Organic Framework of Distorted NbO-like Net (pzdc = Pyrazine-2,3-dicarboxylato)," Chemistry Letters vol. 32, No. 9, pp. 796-797, Aug. 4, 2003.

Jason K. Holt, et al., "Fabrication of a Carbon Nanotube-Embedded Silicon Nitride Membrane for Studies of Nanometer-Scale Mass Transport," American Chemical Society, Nano Letters 2004, vol. 4, No. 11, pp. 2245-2250.

Jessee L.C. Rowsell, et al., "Metal-organic frameworks: a new class of porous materials," Microporous and Mesoporous Materials 73, 2004, pp. 3-14.

Suman Mukhopadhyay, et al., "Honeycomb Nets with Interpenetrating Frameworks Involving Iminodiacetato-Copper (II) Blocks and Bipyridine Spacers: Syntheses, Characterization, and Magnetic Studies," Inorganic Chemistry, 2004, 43, pp. 3413-3420.

Mind-Hua Zeng, et al., "Crystal-to-crystal transformations of a microporous metal-organic laminated framework triggered by guest exchange, dehydration and readsorption," Dalton Trans., 2004, pp. 2217-2223.

Junji Ito, et al., "Discrimination of halitosis substance using QCM sensor array and a preconcentrator," Sensors and Actuators B 99 (2004) pp. 431-436.

Qiang Wei, et al., "A manganese metal-organic framework which remains crystalline on desolvation, and which gives insight into the rotational freedom of framework aromatic groups," Microporous and Mesoporous Materials 73 (2004) pp. 97-100.

Xiang-Jun Zheng, et al., "Hydrothermal syntheses, structures and magnetic properties of two transition metal coordination polymers with a square grid framework," Polyhedron 23, (2004) pp. 1257-1262.

Klaus Schlichte, et al., "Improved synthesis, thermal stability and catalytic properties of the metal-organic framework compound $Cu_3(BTC)_2$," Microporous and Mesoporous Materials 73 (2004) pp. 81-88.

Danil N. Dybtsev, et al., "Rigid and flexible: A Highly Porous Metal-Organic Framework with Unusual Guest-Dependent Dynamic Behavior," Angew. Chem. Int. Ed. (2004) 43, pp. 5033-5036.

Danil N Dybtsev, et al., "Three-dimensional metal-organic framework with (3,4)-connected net, synthesized from an ionic liquid medium," Chem. Commun. (2004) pp. 1594-1595.

Ryo Kitaura, et al., "Rational Design and Crystal Structure Determination of a 3-D Metal-Organic Jungle-Gym-Like Open Framework," Inorganic Chemist (2004), vol. 43, No. 21, pp. 6522-6524.

Filipe A. Almeida Paz, et al., "Synthesis and Characterization of a Novel Cadmium-Organic Framework with Trimesic Acid and 1,2-Bis(pyridl)ethane," Inorganic Chemistry (2004),vol. 43, No. 13, pp. 3948-3954.

Eithne Tynan, et al., "Solvent templated synthesis of metal-organic frameworks: structural characterization and properties of the 3D network isomers ([Mn(dcbp)] · ½ DMF)$_n$ and {[Mn(dcbp)] · 2H₂O}$_n$," Chem. Comm. (2004), pp. 776-777.

Haitao Xu, et al., "Two new microporous coordination polymers constructed by ladder-like and ribbon-like molecules with cavities," Journal of Molecular Structure 693 (2004) pp. 11-15.

Cheng-Yong Su, et al., "A three-dimensional, noninterpenetrating metal-organic framework with the moganite topology: a simple (4². 6².8²)(4.6⁴.8)₂ net containing two kinds of topologically nonequivalent points," Inorganic Chemistry Communication (2004), vol. 43, pp. 6881-6883.

Cheng-Yong Su, et al., "Exceptionally stable, hollow tubular metal-organic architectures: synthesis, characterization, and solid-state transformation study," Journal of the American Chemical Society, (2004) vol. 126, pp. 3576-3586.

Giannis S. Papaefstathiou, et al., "A 2D metal-organic framework with two different rhombus-shaped cavities: a rare example of a (4,4)-net with alternating metal and organic nodes," Microporous and Mesoporous Materials 71(2004) pp. 11-15.

Yan Bai, et al., "A three dimensional porous metal-organic framework [Fe₄L₆ · (DMF)₃ · (H₂O)₁₀] constructed from neutral discrete Fe₄L₆ pyramids [H₂L = 1,3-benzohydroxamix acid]," Chem, Commun., (2004) pp. 186-187.

M. J. Rosseinsky, "Recent developments in metal-organic framework chemistry: design, discovery, permanent porosity and flexibility," Microporous and Mesoporous Materials 73(2004), pp. 15-30.

Hye Jin Choi, et al., "Dynamic and redox active pillared bilayer open framework: single-crystal-to-single crystal transformations upon guest removal, guest exchange, and framework oxidation," Journal of the American Chemical Society, (2004), vol. 126, pp. 15844-15851.

Ashleigh J. Fletcher, et al., "Adsorption of gases and vapors on nanoporous $Ni_2(4,4'$- bipyridine$)_3(NO_3)_4$ metal-organic framework materials templated with methanol and ethanol: structural effects in adsorption kinetics," Journal of the American Chemical Society, (2004), vol. 126, pp. 9750-9759.

Xinlong Wang, et al., "Designed double layer assembly: a three-dimensional open framework with two types of cavities by connection of infinite two-dimensional bilayer," Chem. Comm., (2004), pp. 378-379.

Yaqin Guo, et al., "Synthesis and Crystal Structure of a Novel Three-Dimensional Supramolecular Network Containing One-Dimensional Honeycomb-Like Channels," Inorganica Chimica Act vol. 357, (2004) pp. 4582-4586.

Liying Duan, et al., "Hydrothermal synthesis and crystal structures of two novel rare earth coordination polymers based on pyridine-2,6-dicarboxylic acid," Journal of Molecular Structure 689, (2004) pp. 269-274.

Sujit K. Ghosh, et al., "Puckered-boat conformation hexameric water clusters stabilized in a 2D metal-organic framework structure built from Cu(II) and 1,2,4,5-benzenetetracarboxylic acid," Inorganic Chemistry, (2004), vol. 43, pp. 5180-5182.

Hee K. Chae, et al., "A route to high surface area, porosity and inclusion of large molecules in crystals," Nature, vol. 427, Feb. 2004, pp. 523-527.

Xuebo Zhao, et al., "Hysteretic adsorption and desorption of hydrogen by nanoporous metal-organic frameworks," Science, vol. 306, Nov. 5, 2004, pp. 1012-1015.

Dat T. Tran, et al., "Open Metal-Organic Framework Containing Cuprate Chains," Inorganic Chemistry, vol. 44, No. 18, 2005, pp. 6192-6196.

Chia-Jung Lu, et al., "First-Generation Hybrid MEMS Gas Chromatograph," Lab on a Chip, 2005, 5, pp. 1123-1131.

C.E. Davis, et al., "Enhanced Detection of m-xylene Using a Preconcentrator with a Chemiresistor Sensor," Sensors and Actuators B 104, 2005, pp. 207-216.

A.T. Carvalho, et al., "Improvement on Organic Compound Adsorption and/or Detection by Using Metallic Thin Films Deposited onto Highly Rough Silicon Substrates," Sensors and Actuators B 108, 2005, pp. 947-954.

Yanjun Tang, et al., "A Micro-post Preconcentrator for a Microscale Gas Chromatography System," 2005 Micro Total Analysis Systems Conference (Boston, MA, Oct. 2005); Transducers Research Foundation Proceedings of the 2005 Micro Total Analysis Systems Conference, p. 660-662 (2005).

Bing-Bing Ding, et al., "Pillared-Layer Microporous Metal-Organic Frameworks Constructed by Robust Hydrogen Bonds. Synthesis, Characterization, and Magnetic and Adsorption Properties of 2,2'-Biimidazole and Carboxylate Complexes," Inorganic Chemist vol. 44, No. 224, 2005, pp. 8836-8845.

Qianrong Fang, et al., "A metal-organic framework with the ziolite MTN Topology containing large cages of vol. 2.5 nm³," Angew. Chem. Int. Ed. 2005, 44, pp. 3845-3848.

Banglin Chen, et al., "High H₂ adsorption in a microporous metal-organic framework with open metal sites," Angew. Chem. Int. Ed. 2005, 44, pp. 4745-4749.

Drew L, Murphy, et al., "A chiral, heterometallic metal-organic framework derived from a tris(chelate) coordination complex," Chemist Communication, 2005, pp. 5506-5508.

Radu Custelcea, et al., "A metal-organic framework functionalized with free carboxylic acid sites and its selective binding of a Cl(H₂O)₄—cluster," J. Am. Chem. Soc. 2005, 127, pp. 16362-16363.

Thomas Devic, et al., "MIL-103, A 3-D lanthanide-based metal organic framework with large one-dimensional tunnels and a high surface area," J. Am. Chem. Soc. 2005, 127, pp. 12788-12789.

Jarrod F. Eubank, et al,, "Terminal co-ligand directed synthesis of a neutral, non-interpenetrated (10,3)-αmetal-organic framework," Chemical Communication, 2005, pp. 2095-2097.

Lei Wang, et al., "Two-dimensional metal-organic framework constructed from 4,4'-bipydine and 1,2,4-benzenetricarboxylate: synthesis, structure and magnetic properties," Journal of Solid State Chemistry, 178 (2005) pp. 3359-3365.

Ru-Qiang Zou, et al., "A hydrogen-bonded 3D coordination network of $Co^{II}$ with 4-($p$-benzoxy)-1,2,4-triazole: hydrothermal synthesis, characterization, crystal structure and emission property," Journal of Molecular Structure 737 (2005) pp. 125-129.

Jun Hong, "[$Zn_2$(BTDA)(bpy)($H_2O$)]•0.5bpy: a new three-dimensional metal-organic framework constructed from flexible and rigid mixed ligands," Journal of Molecular Structure 752 (2005) pp. 166-169.

Henrik Fano Clausen, et al., "Solvothermal synthesis of new metal organic framework structures in the zinc-terephthalic acid-dimethyl formamide system" Journal of Solid State Chemist 178, (2005) pp. 3342-3351.

Giovanni Garberoglio, et al., "Adsorption of gases in metal organic materials: comparison of simulations and experiments," Journal of Physical Chemist B (2005) 109, pp. 13094-13103.

Gregory J. Halder, et al., "In situ single-crystal x-ray diffraction studies of desorption and sorption in a flexible nano porous molecular framework material," Journal of the American Chemical Society (2005), 127, pp. 7891-7900.

Ryo Kitaura, et al., "Formation and characterization of crystalline molecular arrays of gas molecules in a 1-dimensional ultramicropore of a porous copper coordination polymer," Journal of Physical Chemist B, (2005) 109, pp. 23378-23385.

Zheming Wang, et al., "Synthesis and characterization of a porous magnetic diamond framework, $Co_3(CHOO)_6$, and its $N_2$ sorption characteristic," Inorganic Chemist (2005), vol. 44, No. 5, pp. 1230-1237.

Hendrik Dathe, et al., "Metal organic frameworks based on $Cu^{2+}$ and benzene-1,3,5-tricarboxylate as host for $SO_2$ trapping agents," C. R. Chimie 8 (2005) pp. 753-763.

Jeong Yong Lee, et al., "Gas sorption properties of microporous metal organic frameworks," Journal of Solid State Chemist 178 (2005) pp. 2527-2532.

Jeong Yong Lee, et al., "Achieving high density of adsorbed hydrogen in microporous metal organic frameworks," Advanced Materials (2005) vol. 17, pp. 2703-2706.

Carine Livage, et al., "A three-dimensional metal-organic framework with an unprecedented octahedral building unit," Angew. Chem. Int. Ed. (2005) vol. 44, pp. 6488-6491.

Andrea M. Goforth, et al., "Connecting small ligands to generate large tubular metal-organic architectures," Journal of Solid State Chemist 178, (205) pp. 2511-2518.

Linhua Xie, et al., "A three-dimensional porous metal-organic framework with the rutile topology contructed from triangular and distorted octahedral building blocks," Chem. Comm., (2005) pp. 2402-2404.

Giannis S. Papaefstathiou, et al,, "Design and construction of a 2D metal organic framework with multiple cavities: a nonregular net with a paracyclophane that codes for multiply fused nodes," Journal of the American Chemical Society, vol. 127, No. 41 (2005) pp. 14160-14161.

O. I. Lebedev, et al., "First direct imaging of giant pores of the metal-organic framework MIL-101," Chemistry Materials, (2005), vol. 17, pp. 6525-6527.

Dat T. Tran, et al., "Open metal-organic framework containing cuprate chains," Inorganic Chemistry, (2005) vol. 44, No. 18, pp. 6192-6196.

Ashleigh J. Fletcher, et al., "Flexibility in metal-organic framework materials: Impact on sorption properties," Journal of Solid State Chemist 178, (2005) pp. 2491-2510.

Tatsuhiko Sagara, et al., "New isoreticular metal-organic framework materials for high hydrogen storage capacityj," The Journal of Chemical Physics 123, 214707 (2005), pp. 1-6.

Tatsuhiko Sagara, et al., "Binding energies of hydrogen molecules to isoreticular metal-organic framework materials," The Journal of Chemical Physics 123, 014701 (2005), pp. 1-4.

Eun Young Lee, et al,, "Multifunctionality and crystal dynamics of a highly stable, porous metal-organic framework [$Zn_4$O(NTB)$_2$]" Journal of the American Chemical Society (2005) vol. 127, pp. 6374-6381.

Xiao-Jun Zhao et al., "A three-dimensional zinc trimesate framework: [($CH_3$)$_2$$NH_2$] [$Zn(C_9H_3O_6)$] • ($C_3H_7NO$)," Applied Organometallic Chemistry (2005), vol. 19, pp. 694-695.

D. Maspoch, et al., "EPR characterization of a nanoporous metal-organic framework exhibiting a bulk magnetic ordering," Journal of Physics and Chemistry of Solids, (2005), vol. 65, pp. 819-824.

Xin-Long Wang, et al., "An unprecedented eight-connected self-penetrating network based on pentanuclear zinc cluster building blocks," Chem. Communication, (2005), pp. 4789-4791.

Xiuli Bai Yangguang Li, et al., "A novel three-dimensional hybrid framework based on fishbone-like copper halide inorganic units," Inorganica Chimica Acta 358, (2005), pp. 2571-2574.

Jorge Gonzalez, et al., "Deuterium NMR studies of framework and guest mobility in the metal-organic framework compound MOF-5, $Zn_4O(O_2CC_6H_4CO_2)_3$," Microporous and Mesoporous Materials 84, (2005), pp. 97-104.

Ru-Qiang Zou, et al., "Rational assembly of a 3D metal-organic framework for gas adsorption with predesigned cubic building blocks and 1D open channels," Chem, Commun., (2005) pp. 3526-3528.

Yi-Hang Wen, et al., Hydrothermal syntheses, crystal structures and characterizations of three new copper coordination polymers, Inorganica Chimica Acta 358 (2005) pp. 3347-3354.

Sujit K. Ghosh, et al., "Infinite chains of quasi-planar hexameric water clusters stabilized in a metal-organic framework built from $Co^{II}$ and pyrazine-2,3,5,6-tetracarboxylic acid," Eur. Journal of Inorganic Chemistry (2005), pp. 4880-4885.

Miguel Fuentes-Cabrera, et al., "Electronic structure and properties of isorcticular metal-organic frameworks: the case of $M$-IRMOF1 ($M$=Zn, Cd, Be, Mg, and Ca)," The Journal of Chemical Physics vol. 123, (2005), 124713, pp. 1-5.

Jianghua He, et al., "Synthesis, structure, and luminescent property of a heterometallic metal-organic framework constructed from rod-shaped secondary building blocks," Inorganic Chemistry, (2005) vol. 44, pp. 9279-9282.

Andrew R. Millward, et al., "Metal-organic frameworks with exceptionally high capacity for storage of carbon dioxide at room temperature," Journal of the American Chemical Society (2005), vol. 127, pp. 17998-17999.

Banglin Chen, et al., "Transformation of a metal-organic framework from the NbO to PtS net," Inorganic Chemistry, (2005), vol. 44, pp. 181-183.

Zhenqiang Wang, et al., "Ternary nets formed by self-assembly of triangles, squares, and tetrahedra," Angew. Chem. Int. Ed., (2005), vol. 44, pp. 2877-2880.

T, Yildirim, et al., "Direct observation of hydrogen adsorption sites and nanocage formation in metal-organic frameworks," Physical Review Letters, Nov. 18, 2005, vol. 95, 215504 pp. 1-4.

Danil N. Dybtsev, et al, "A Homochiral Metal-Organic Material with Permanent Porosity, Enantioselective Sorption Properties, and Catalytic Activity," Agnew, Chem. Int. Ed., 2006, 45, pp. 916-920.

Flachsbart, et al., "Design and fabrication of a multilayered polymer microfluidic chip with nanofluidic interconnects via adhesive contact printing," Lab-On-A-Chip, 6, 667-674, 2006.

Timothy M. Long, et al., "Water-Vapor Plasma-Based Surface Activation for Trichlorosilane Modification of PMMA," Langmuir vol. 22, No. 9, 2006, pp. 4104-4109.

Eliphas Wagner Simoes, et al., "Study of preconcentration of non-polar compounds in microchannels with constrictions," Sensors and Actuators B 115, 2006, pp. 232-239.

Ru-Qiang Zou, et al., "Strong fluorescent emission of a new fourfold-interpenetrated diamondoid metal-organic framework of zinc(II) urocanate with one-dimensional open channels," Microporous and Mesoporous Materials 91, 2006, 233-237.

Tong Ye, et al., "Ferroeletric Metal-organic framework with a high dielectric constant," JACS, 2006, 128, pp. 6554-6555.

Banglin Chen, et al., "A microporous metal-organic framework for gas-chromatographic separation of alkanes," Angew. Chem. Int. Ed. 2006, 45, 1390-1393.

Pascal D. C. Dietzel, et al., "Hydrogen adsorption in a nickel based coordination polymer with open metal sites in the cylindrical cavities of the desolvated framework," Chemical Communication, 2006, pp. 959-961.

Lei Wang, et al., "Highly stable chiral cadmium 1,2,4-benzenetricarboxylate: Synthesis, structure, and NLO and fluorescence properties," Inorganic Chemistry, vol. 45, No. 6, 2006, pp. 2474-2478.

Feng Zheng, et al., "Single-Walled Carbon Nanotube Paper as a Sorbent for Organic Vapor Preconcentration," Analytical Chemistry, 2006, vol. 78, No. 7, pp. 2442-2446.

Rasmus Damgaard Poulsen, et al., "Solvothermal synthesis, multi-temperature crystal structures and physical properties of isostructural coordination polymers, $2C_4H_{12}N^+-[M_3(C_8H_4O_4)_4]^{2-}3C_5H_{11}NO$ $M=$ Co, Zn," Acta Crystallography (2006) B62, pp. 245-254.

Piotr Krawiec, et al., "Improved hydrogen storage in the metal-organic framework $Cu_3(BTC)_2$," Advanced Engineering Materials (2006) 8 No. 4, pp. 293-296.

Cameron J. Kepert, "Advanced functional properties in nanoporous coordination framework materials," Chemical Communication, (2006) pp. 695-700.

Long Pan, et al., "Separation of hydrocarbons with a microporous metal-organic framework," Angew. Chem. Int. Ed. (2006) vol. 45, pp. 616-619.

Shuangquan Zang, et al., "Interweaving of triple-helical and extended metal-o-metal single-helical chains with the same helix axis in a 3D metal-organic framework," Inorganic Chemist (2006), vol. 45, No. 10, pp. 3855-3857.

U. Mueller, et al., "Metal-organic framework—prospective industrial applications," Journal of Materials Chemistry, (2006) vol. 16, pp. 626-636.

Frank Stallmach, et al., "NMR studies on the diffusion of hydrocarbons on the metal-organic framework material MOF-5," Angew. Chem. Int. Ed. (2006), vol. 45, pp. 2123-2126.

Gyungse Park, et al., "Solvothermal synthesis, crystal structure, and magnetic properties of $[Co_3(SDA)_3(DMF)_2]$; 2-D layered metal-organic framework derived from 4,4' stilbenedicarboxylic acid ($H_2SDA$)," Bull. Korean Chem. Soc. (2006)., vol. 27, No. 3 .443-446.

Enrica Biemmi, et al,, "Synthesis and characterization of a new metal organic framework structure with a 2D porous system: ($H_2Net_2$) $[Zn_3(BDC)_4]$ 3DEF," Solid State Sciences 8, (2006), pp. 363-370.

Suzy Surble, et al., "An EXAFS study of the formation of a nanoporous metal-organic framework: evidence for the retention of secondary building units during synthesis," Chem Commun., (2006) pp. 1518-1520.

Cheng-Zhi Xie, et al., "A novel 3D $Cu^I$ metal-organic framework with middle-size channels despite the sixfold $ThSi_2$ interpenetrating topological structure," Eur. Journal of Inorganic Chemistry (2006) pp. 1337-1340.

Subhadip Neogi, et al., "Metal-organic frameworks of lanthanide (III) ions with a pod and bearing terminal carboxylates: Identification of water clusters of different nuclearity," Polyhedron 25 (2006) pp. 1491-1497.

C. Prestipino, et al. "Local structure of framework Cu(II) in HKUST-1 metallorganic framework: spectroscopic characterization upon activation and interaction with adsorbates," Chemical Materials, (2006), vol. 118, pp. 1337-1346.

Andrea C. Sudik, et al., "A metal-organic framework with a hierarchical system of pores and tetrahedral building blocks," Angew. Chem. Int. Ed., (2006), vol. 45, pp. 2528-2533.

Antek G. Wong-Foy, et al., "Exceptional $H_2$ saturation uptake in microporous metal-organic frameworks," Journal of the American Chemical Society (2006), vol. 128, pp. 3494-3495.

Jianghua He, et al., "Three metal-organic frameworks prepared from mixed solvents of DMF and HAc," Microporous and Mesoporous Materials, (2006), vol. 90, pp. 145-152.

Byunghoon Bae, et al., "A Touch-Mode Capacitance Microvalve Equipped with High Speed and Pressure Microsecond Switching Performance," MEMS 2006, Istanbul, Turkey, Jan. 22-26, 2006, pp. 766-769.

Patrick R. Lewis, et al., "Recent Advancements in the Gas-Phase MicroChemLab," IEEE Sensors Journal, vol. 6, No. 3, Jun. 2006, pp. 784-795.

Shaurya Prakash, et al., "Electroosmotic Flow in 'Click' Surface Modified Microfluidic Channels," Proceedings of ASME ICNMM2006, $4^{th}$ International Conference on Nanochannels, Microchannels and Minichannels, Jun. 19-21, 2006, Limerick, Ireland, Paper No. ICNMM2006-96153.

J. Yeom, et al., "Design and Characterization of Micropost-Filled Reactor for the Minimal Pressure Drop and Maximal-Surface-Area-to-Volume Ratio," Proceedings of IMECE 2006, 2006 ASME International Mechanical Engineering Congress and Exposition, Nov. 5-10, 2006, Chicago, Illinois, USA, IMECE2006-15836.

Zhuojia Lin, et al., "Microwave-Assisted Synthesis of Anionic Metal-Organic Frameworks Under Ionothermal Conditions," The Royal Society of Chemistry 2006, Chem. Commun., 2006, pp. 2021-2023.

N. Rajic, et al., "An Evidence for a Chain to Network Transformation During the Microwave Hydrothermal Crystallization of an Open-Framework Zinc Terephthalate," J. Porous Mater. 2006, vol. 13: pp. 153-156.

Ioana Voiculescu, et al., "Micropreconcentrator for Enhanced Trace Detection of Explosives and Chemical Agents," IEEE Sensors Journal, vol. 6, No. 5, Oct. 2006, pp. 1094-1104.

Bochobza-Degani, O. et al., On the effect of residual charges on the pull-in parameters of electrostatic actuators, Sensors and Actuators A 97-98:563-568 (2002).

Bosch, D. et al., A silicon microvalve with combined electromagnetic/electrostatic actuation, Sensors and Actuators 37-38:684-692 (1993).

Castañer, L. M. et al., Pull-in time—energy product of electrostatic actuators: comparison of experiments with simulation, Sensors and Actuators, 83:263-269 (2000).

Legtenberg, R. et al., Electrostatic Curved Electrode Actuators, Journal of Microelectromechanical Systems 6(3):257-265 (1997).

Messner, S. et al., 3-way silicon microvalve for pneumatic applications with electrostatus actuation principle, Microfluid Nanofluid 89-96 (2006).

Messner, S. et al., Electrostatic driven 3-way silicon microvalve for pneumatic applications, IEEE 88-91 (2003).

Oberhammer, J. et al., Design and fabrication aspects of an S-shaped film actuator based DC to RF MEMS switch, Journal of Microelectromechanical Systems 13(3):421-428 (2004).

Ohnstein, T. et al., Micromachined silicone microvalve, Proc. IEEE Micro Electro Mechanical Systems, An Investigation of Micro Structures, Sensors, Actuators, Machines and Robots, Napa Valley, CA 95-98 (1990).

Philpott, M. L. et al., Switchable electrostatic micro-valves with high hold-off pressure, Technical Digest of the 2000 Solid-State Sensor and Actuator Workshop, 226-229.

Sato, K. et al., An electrostatically actuated gas valve with an S-shaped film element, J. Micromech. Microeng. 4:205-209 (1994).

Schaible, J. et al., Electrostatic microvalves in silicon with 2-way-function for industrial applications, The $11^{th}$ International Conference on Solid-State Sensors and Actuators, Munich, Germany 928-931 (2001).

Shikida, M. et al., Characteristics of an electrostatically-driven gas valve under high-pressure conditions, Center for Materials Processing Technology 235-240 (1994).

Shikida, M. et al., Electrostatically driven gas valve with high conductance, Journal of Microelectromechanical Systems, 3(2):76-80 (1994).

Shikida, M. et al., Fabrication of an S-shaped microactuator, Journal of Microelectromechanical Systems, 6(1):18-24 (1997).

Shikida, M. et al., Micromachined S-shaped actuator, Sixth International Symposium on Micro Machine and Human Science 167-172 (1995).

Shikida, M. et al., Response time measurement of electrostatic S-shaped film actuator related to environmental gas pressure conditions, IEEE 210-215 (1996).

Vandelli, N. et al., Development of a MEMS microvalve array for fluid flow control, Journal of Microelectromechanical Systems 7(4):395-403 (1998).

Yang, X. et al., An electrostatic, on/off microvalve designed for gas fuel delivery for the MIT microengine, Journal of Microelectromechanical Systems, 13(4):660-668 (2004).

Huff et al., A pressure-balanced electrostatically-actuated microvalve, Technical Digest, 1990 Solid-State Sensor and Actuator Workshop, pp. 123-127 (1990).

WATER REPELLENT METAL-ORGANIC FRAMEWORKS, PROCESS FOR MAKING AND USES REGARDING SAME

CROSS-REFERENCES TO RELATED APPLICATIONS

This application claims priority to and the benefit under 35 U.S.C. §119(e) to provisional application 61/043,288, filed Apr. 8, 2008, the disclosure of which is expressly incorporated herein by reference in its entirety.

STATEMENT AS TO RIGHTS TO INVENTIONS MADE UNDER FEDERALLY SPONSORED RESEARCH AND DEVELOPMENT

This invention was made, at least in part, with U.S. government support under U.S. Air Force Grant No. FA8650-04-1-7121, awarded by the Defense Advanced Research Projects Agency (DARPA). The U.S. government has certain rights in the invention.

BACKGROUND OF THE INVENTION

1. Field of the Invention

The invention generally relates to water-repellent metal organic framework (MOF) molecules and methods for synthesizing such MOFs, such as, for example microwave assisted synthesis.

2. Related Art

MOFs are organometallic nanoporous structures with high surface area and tailorable selectivity. MOFs may have a cubic crystalline structure that is formed by copolymerization of metals or metal oxides with organic ligands, resulting in metal-oxide clusters connected by organic linkers. FIG. 1 is a diagram of a typical MOF's crystalline structure 10 including metal or metal oxides, here shown as polyhedrons 12, having polymer ligands 14 extending between them. This highly ordered structure facilitates the creation of interior pores and channels. MOFs are known to have about 0.3 nm to about 3 nm pores.

MOFs are thermally robust and in many cases have extremely high porosity. Potential applications for MOFs include gas storage, adsorbents, and catalysts as described in detail in U.S. application Ser. No. 11/539,405, which is expressly incorporated by reference herein in its entirety. Applicants have discovered that certain MOFs have properties that make them highly advantageous as preconcentrators of analytes, including, for example, a high sorption capacity due to their high surface area, a high selectivity to specific analytes, an inert nature which does not decompose the analyte, a thermal stability, which result in unexpectedly high gains in detection, and as further described in U.S. application Ser. No. 11/539,405. Accordingly, MOFs are used to selectively sorb specific analytes in a preconcentrator. MOFs may be used in particle or pellet form, or they may be incorporated into a film inside a preconcentrator. Once the analytes are fully sorbed by the MOFs, the analytes can be released, for example, by thermal desorption. The analytes can then be purged and transferred from the preconcentrator to a detector.

One disadvantage associated with currently available MOFs is their lack of stability and resultant decrease in surface area when exposed to environmental conditions having greater than about 4% water present. Indeed, studies have indicated that water molecules attack the coordination bonds between the metal and organic ligands. Thus, MOF applications may be adversely affected under the most common environmental conditions.

One way to overcome this disadvantage is to fabricate MOFs by incorporating water repellent functional groups onto the ligand to increase the stability of the MOF when exposed to environmental conditions having greater than about 4% water present. This may be accomplished by building porous frameworks with covalent bonds using well-defined organic ligands. But, due to the high reactivities of the organic ligands, their synthesis requires complex processes and demanding crystallization conditions; thus, making this synthesis method undesirable. As an alternative, the MOF framework may be built with ligands using coordinate bonding. Although coordination bonding is not as strong as covalent bonding, it requires milder conditions to create the framework and offers a larger variety of building blocks (e.g., terephthalic acid with different functional groups) that can be used to build the framework relative to building the framework using covalent bonds.

MOF frameworks using coordination bonds may be synthesized using either a simple solvothermal, microwave-assisted solvothermal, or hydrothermal synthesis method, for example, as disclosed in Applicants' application Ser. No. 11/785,102, which is expressly incorporated by reference herein in its entirety. Solvothermal synthesis is a method where ligands for MOF crystal formation are heated in a solvent other than water at high vapor pressure. In hydrothermal synthesis, ligands for MOF crystals are heated in water. Hydrothermal synthesis is suitable when the ligand is soluble in water. In both conventional solvothermal and hydrothermal synthesis, a solution with MOF ligands is typically maintained at a predetermined equilibrium temperature and pressure for an extended period to induce crystallization.

BRIEF SUMMARY OF THE INVENTION

The invention provides novel water-repellent MOFs and processes for synthesizing such MOFs by incorporating water repellent functional groups onto the organic ligands to increase the stability of the MOF when exposed to water. The water-repellent functional groups prevent water from entering the cavities of the MOF. The MOFs of the invention provide many advantages over conventionally available MOFs such as improved MOF stability when exposed to environmental condition. In particular, having greater than about 4% water present. The MOFs may also be non-isoreticular to lower the production cost, and allow a greater number of analytes to be adsorbed. The invention may be implemented in a number of ways.

According to one aspect of the invention a metal organic framework (MOF) may include a plurality of metals and/or metal oxides and a plurality of ligands arranged to form a crystalline structure having a surface area of at least about 100 m$^2$/gm, wherein said plurality of ligands have a structure of Formula I,

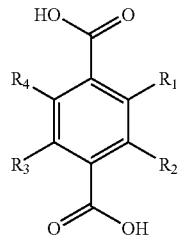

Formula 1 wherein $R_1$-$R_4$ is $DY_3$ or A-$DY_3$ or A-B-$DY_3$, where A is O or S and B is $DY_2$ or O or S, each D is independently C or Si, each Y is independently hydrogen, fluorine, chlorine, or bromine, with the provisos that (i) at least one of A or B must be $DY_2$ in A-B-$DY_3$ and (ii) when D in $DY_2$ is Si, Y is hydrogen, chlorine, or fluorine. The MOF may be non-isoreticular.

The MOF metal may include magnesium, cadmium, beryllium, copper, terbium, gadolinium, iron, nickel, cobalt, silver and zinc. The metal oxide may include magnesium oxide, cadmium oxide, beryllium oxide, copper oxide, terbium oxide, gadolinium oxide, iron oxide, nickel oxide, cobalt oxide, silver oxide and zinc oxide.

The crystalline structure may be a non-linear structure. The non-linear structure may be cubic, spherical, oval, elliptical, fan-shaped, plate-shaped, rectangular, hexagonal, needle, rod, and irregularly shaped.

The crystalline structure has a plurality of pores. The pores have a size in a range of about 1 nm to about 3 nm. The X-ray powder diffractometry (XRPD) spectrum of the MOF does not significantly shift when exposed to water vapor for greater than about 1 hour, where the XPDP of the MOF before and after exposure to water vapor is substantially unchanged. The MOF may have a plurality of macropores. The MOF may include a plurality of particle having a diameter less than about 40 nm.

The MOF metal may be zinc and $R_1$ may be a methyl, ethyl, or trifluoromethyl, 1,1,1-trifluoroethyl, or trifluoromethoxy group and $R_2$, $R_3$, and $R_4$ may be hydrogen. The MOF metal may be zinc and $R_1$ and $R_3$ may be methyl, ethyl, or trifluoromethyl, 1,1,1-trifluoroethyl, or trifluoromethoxy group and $R_2$ and $R_4$ may be hydrogen. The MOF metal may be zinc and $R_1$ and $R_3$ may be methyl groups and $R_2$ and $R_4$ may be hydrogen. The MOF metal may be copper and $R_1$ and $R_3$ may be methyl or ethyl groups and $R_2$ and $R_4$ may be hydrogen. The MOF metal may be copper and $R_1$ and $R_3$ may be methoxy groups and $R_2$ and $R_4$ may be hydrogen. The MOF metal may be cadmium and $R_1$ and $R_3$ may be methoxy groups and $R_2$ and $R_4$ may be hydrogen.

The MOF may be used a sorbent of analyte in a collection system. The collection system may include one of a preconcentrator, micropreconcentrator, personal respirator, and dosimeter. The preconcentrator or micropreconcentrator may be a purge and trap system, microelectromechanical (MEMS) valve system, array of microstructures, dosimeter, disc, pellet, or swab.

According to a further aspect of the invention, a process for synthesizing a water-repellent MOF having a crystalline structure with a surface area of greater than about 100 $m^2$/gm may include removing the impurities from an organic ligand to provide a pre-treated organic ligand, dissolving a metal and/or metal oxide and the pre-treated organic ligand in a solvent to provide a solution, subjecting the solution to microwaves for a time sufficient to form crystals of the water-repellent MOF. The process may further include removing the metal impurities from the water repellent MOF. The metal impurities may be removed by extracting them into an soxhlet extractor solvent using a soxhlet extraction apparatus. The soxhlet extractor solvent may be $CH_2Cl_2$.

The MOF metal may include magnesium, cadmium, beryllium, copper, terbium, gadolinium, iron, nickel, cobalt, silver and zinc. The metal oxide may include magnesium oxide, cadmium oxide, beryllium oxide, copper oxide, terbium oxide, gadolinium oxide, iron oxide, nickel oxide, cobalt oxide, silver oxide and zinc oxide.

The organic ligand may include terephthalic acid, naphthalene dicarboxylic acid, biphenyl-dicarboxylic acid, benzene tricarboxylic, di(carboxyphenyl)benzene, imidazole, benzimidazole, alkane dicarboxylic acid, alkene dicarboxylic acid, and alkyne dicarboxycylic acid.

The impurities may be removed by a method such as contacting the ligand with a chelating resin, soxhlet extraction, liquid-liquid extraction, evaporation and precipitation, and removing metal by washing.

According to another aspect of the invention, a process for synthesizing a water-repellent metallic organic framework (MOF), having a crystalline structure having a surface area of greater than about 100 $m^2$/gm, includes dissolving zinc nitrate hexahydrate and 2-trifluoromethoxy terephthalic acid in a solvent to provide a solution; sealing the dissolved solution in a vessel; and heating the vessel in a microwave oven for a time sufficient to form crystals of the water-repellent MOF. The reaction time may be for about 80 seconds. The crystalline structure may be cubic and the crystals in the heating step may have a size in a range of about 4 μm to about 7 μm.

According to a further aspect of the invention, a process for synthesizing a water-repellent metallic organic framework (MOF), having a crystalline structure having a surface area of greater than about 100 $m^2$/gm, includes dissolving zinc nitrate hexahydrate and 2,5-dimethylterephthalic acid in a solvent; sealing the dissolved solution in a vessel; and heating the vessel in a microwave oven for a time sufficient to form crystals of the water-repellent MOF. The reaction time may be for about 30 seconds. The crystalline structure may be cubic and the crystals in the heating step may have a size in a range of about 1 μm to about 3 μm.

According to a yet further aspect of the invention a process for synthesizing a water-repellent metallic organic framework (MOF), having a crystalline structure having a surface area of greater than about 100 $m^2$/gm, includes dissolving cupric nitrate and 2,5-dimethylterephthalic acid in a solvent; sealing the dissolved solution in a vessel; and heating the vessel in a microwave oven for a time sufficient to form crystals of the water-repellent MOF. The reaction time may be for about 30 seconds. The crystalline structure may be irregularly shaped.

According to another aspect of the invention a process for synthesizing a water-repellent metallic organic framework (MOF), having a crystalline structure having a surface area of greater than about 100 $m^2$/gm, includes dissolving cupric nitrate and 2,5-dimethoxyterephthalic acid in a solvent; sealing the dissolved solution in a vessel; and heating the vessel in a microwave oven for a time sufficient to form crystals of the water-repellent MOF. The reaction time may be for a time period of about 30 seconds. The crystalline structure may be fan-shaped.

According to another aspect of the invention a process for synthesizing a water-repellent metallic organic framework (MOF), having a crystalline structure having a surface area of greater than about 100 $m^2$/gm, includes dissolving cadmium nitrate tetrahydrate and 2,5-dimethoxyterephthalic acid in a solvent; sealing the dissolved solution in a vessel; and heating the vessel in a microwave oven for a time sufficient to form crystals of the water-repellent MOF. The reaction time may be for a time period of about 30 seconds. The crystalline structure may be plate-shaped.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification; illustrate embodiments of the invention and together with the detailed description serve to explain the principles of the invention. No attempt is made to show structural details of the invention in more detail than may be necessary for a fundamental understanding of the invention and various ways in which it may be practiced.

DETAILED DESCRIPTION OF THE INVENTION

Figure 1:
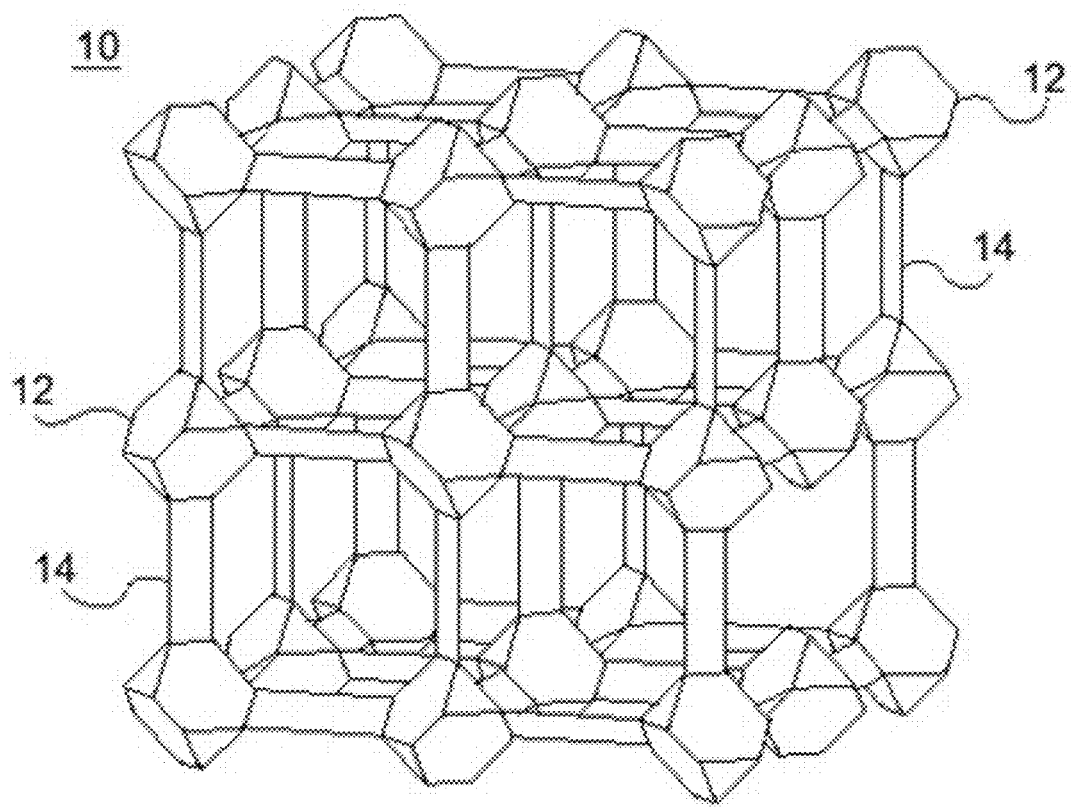
FIG. 1 is a diagram showing a typical crystalline structure of a MOF.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. This, for example, a reference to "a linker" is a reference to one or more linkers and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

DEFINITIONS

TGA is thermogravimetric analysis
XRPD is X-ray powder diffractometry
DMMP is Dimethyl methylphosphonate
$E_T^N$ is normalized solvent polarity
SCCM is standard cubic centimeters per minute
DEF is diethyl formamide
DMF is dimethyl formamide The term "metal-organic framework," abbreviated "MOF," as used herein, refers to a one, two, or three dimensional polymer including both organic and metal or metal oxide structural units, where at least one of the metal units is bonded to at least one bi-, tri- or poly-dentate organic unit.

The terms "halo" and "halogen" are used in the conventional sense to refer to a chloro, bromo, fluoro or iodo substituent. The term "haloalkyl" or "halogenated" refers to an alkyl group in which at least one of the hydrogen atoms of the alkyl group has been replaced with a halogen atom.

The term "ligand" refers to organic ligand compounds containing one or more functional groups attached suitable for chemically binding of a first and second molecule together, and, specifically a first and second molecule that is a metal or metal oxide. The organic ligands may include without limitation, terephthalic acid, naphthalene dicarboxylic acid, biphenyl-dicarboxylic acid benzene tricarboxylic, di(carboxyphenyl)benzene, imidazole, benzimidazole, and alkane, alkene and alkyne dicarboxylic acids. Chemical binding is considered to broadly cover bonding with some covalent character with or without polar bonding and can have properties of ligand-metal bonding along with various degrees of ionic bonding.

The term "non-polar functional group," as used herein, generally refers to any functional group that is capable of preventing water from entering the cavities of the MOF while still allowing other molecules to penetrate into the MOF. The term "functional group," as used herein, may be used interchangeably with the terms "water-repellent function group," or "non-polar functional group." The functional group may be selected based on the composition of the molecule, and specifically may be a functional group such as methoxy, halogenated methoxy, methyl, halogenated methyl, ethyl, halogenated ethyl, halogenated linear hydrocarbons, halogenated branched hydrocarbons, siloxane, perfluorourinated hydrocarbon.

The term "analyte," as used herein, refers to a substance which a laboratory or other entity seeks to detect and/or identify using analytical procedures and/or techniques.

The term "sorption," as used herein, refers to the total effect of atoms, molecules, or ions being incorporated into a material's volume, and/or of atoms, molecules, or ions adhering to a material's surface by any mechanism, including, but not limited to adsorption and absorption.

The term "adsorption," as used herein, refers to the adhesion of an extremely thin layer of atoms, molecules, or ions to the surfaces of solid bodies or liquids with which they are in contact.

The term "absorption," as used herein, refers to a physical or chemical process by which atoms, molecules, or ions enter the volume of a bulk phase material.

The term "sorbent" also is used in its broadest sense to refer to a material that incorporates atoms, molecules, or ions into its volume and/or adheres atoms, molecules, or ions to its surface by "sorption" as defined above. For example, a sorbent that is "highly selective" for substance X relative to substance Y will sorb X at least 100× more effectively than Y.

The term "desorption" refers to a process by which a sorbed material is released from a "sorbent."

The term "highly selective," as used herein, generally refers to at least about 100 times greater selectivity of a sorbent to a desired analyte in a sample, relative to another substance in the sample being analyzed.

The term "isoreticular," as used herein when referring to a MOF, means a MOF that has a single crystalline net, where substantially all of the unit cells have the same chemical structure and substantially the same functional groups. See Yaghi ET AL. U.S. Pat. No. 6,930,193.

The term "non-isoreticular," as used herein when referring to a MOF, means a MOF that is not isoreticular. This may include MOFs that include of a mixture of ligands. This may include MOFs, where different ligands within the structure have different functional groups. This includes MOFs with macropores and MOFs that have been modified to include additional ligands and/or functional groups.

The term "not substantially hinder diffusion," as used herein, refers to a reduction in diffusion of less than a factor of 100. For example, a MOF that does not reduce the diffusion of a target analyte such as hydrogen into the MOF by more than a factor of 100.

The term "macropore," as used herein, refers to a pore with a diameter larger than about 50 nm.

The term "micropore," as used herein, refers to a pore with a diameter less than about 50 nm.

The term "breakthrough volume," as used herein means the volume at which a particular solute pumped continuously through a column will begin to be eluted. It is related to the column volume and the retention factor of the solute. It is used to determine amount of gas (e.g., air) that can be passed over the adsorbent before significant solute is detected at the end of the adsorbent bed.

The invention relates generally to MOF structures and processes for synthesizing MOF structures. The MOFs can be used, for example, preconcentrators, for example. In particular, the invention provides processes for building water-repellent MOF structures by incorporating a water-repellent functional group into the organic ligands of the MOF framework. The water-repellent MOFs of the invention show high moisture stability and have several applications in environmental monitoring According to one embodiment of the invention, the MOFs may have a crystalline structure that is formed by copolymerization of metals or metal oxides with organic ligands, resulting in metal-oxide clusters connected by organic linkers. The metal or metal oxide may include, without limitation, zinc, cadmium, magnesium, beryllium, copper, calcium, terbium, gadolinium, iron, nickel, cobalt, and silver. The MOF may be comprised of organic ligands having the general structure of Formulas 1-3, where at least one of $R_1$, $R_2$, $R_3$, and $R_4$ are non-polar functional groups.

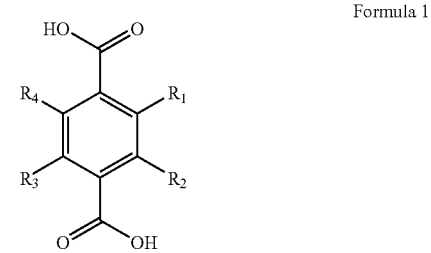

Formula 1

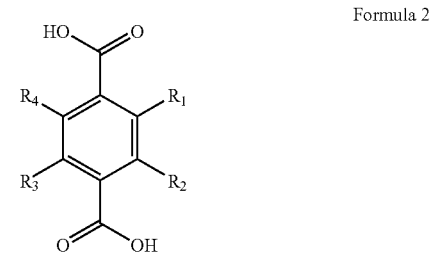

Formula 2

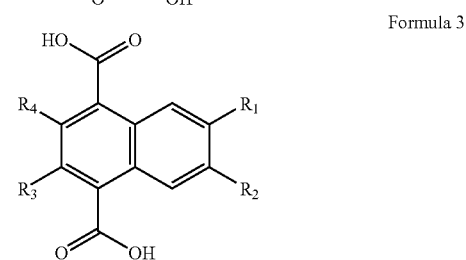

Formula 3

In a more specific embodiment, the organic ligands of Formulas I-III, above, may be defined where $R=DY_3$ or $A-DY_3$ or $A-B-DY_3$, where $A=O$ or $S$ and $B=DY_2$ or $O$ or $S$, each D is independently C or Si, each Y is independently hydrogen, fluorine, chlorine, or bromine, with the provisos that (i) at least one of A or B must be $DY_2$ and (2) when D in $DY_2$ is Si, Y is hydrogen, fluorine, or chlorine.

The MOF may be comprised of organic ligands having the general structure of Formula 4, below, where at least one of $R_1$, $R_2$, and $R_3$ are non-polar functional groups.

Formula 4

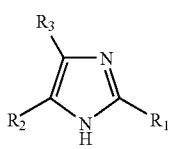

The MOF may be comprised of organic ligands having the general structure of Formula 5, below, where at least one of $R_1$, $R_2$, $R_3$, $R_4$, and $R_5$ are non-polar functional groups.

Formula 5

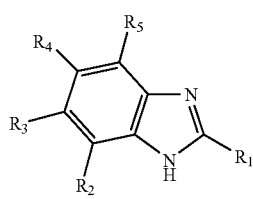

The MOF may be comprised of organic ligands having the general structure of Formula 6, below, where at least one of $R_1$, $R_2$, $R_3$, $R_4$, $R_5$, and $R_6$ are non-polar functional groups.

Formula 6

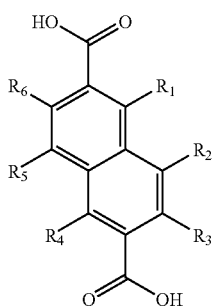

The MOF may be comprised of organic ligands having the general structure of Formula 7, below, where at least one of $R_1$, $R_2$, $R_3$, $R_4$, $R_5$, $R_6$, $R_7$, and $R_8$ are non-polar functional groups.

Formula 7

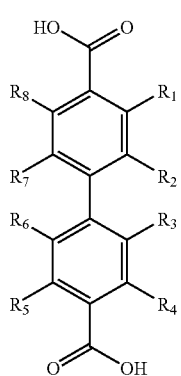

The MOF may be comprised of organic ligands having the general structure of Formula 8, below, where at least one of $R_1$, $R_2$, $R_3$, $R_4$, $R_5$, $R_6$, $R_7$, $R_8$, $R_9$, $R_{10}$, $R_{11}$, and $R_{12}$ are non-polar functional groups:

Formula 8

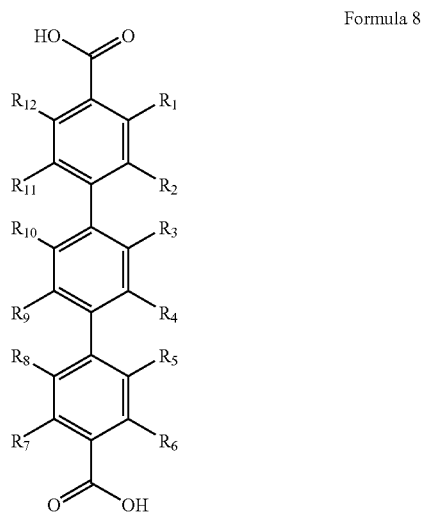

In one aspect of the invention, the MOF may have the structure of Formula 1 wherein at least one of $R_1$ and $R_2$ and at least one of $R_3$ and $R_4$ are non-polar functional groups. In a further aspect of the invention, the MOF may include a combination of organic ligands of any of Formulas 1-8, detailed above.

The water-repellent functional groups or non-polar functional groups, may include, without limitation, trifluoromethoxy, methyl, ethyl, linear hydrocarbons having about 1 to about 4 carbons in length, more preferably about 1 to about 3 carbons in length, and even more preferably about 1 to about 2 carbons in length, branched chain hydrocarbons having about 1 to about 4 in length, and more preferably having about 1 to about 3 carbons in length, and even more preferably having about 1 to about 2 carbons in length, methoxy, halogenated methoxy, halogenated ethoxy, halogenated methyl, halogenated ethyl, halogenated linear hydrocarbons, halogenated branched hydrocarbons, siloxane, perfluorinated carbon. The water-repellent functional groups should not substantially hinder diffusion of target analytes into the MOF.

The water-repellent functional groups may contain three or less carbon atoms and/or oxygen atoms such that the size of the ligand does not substantially hinder the diffusion of analytes such as hydrogen into the MOF.

The water-repellent functional groups may be chosen so that they contain two or less carbon atoms and/or oxygen atoms such that the size of the ligand does not substantially hinder the diffusion of analytes such as hydrogen into the MOF.

The MOFs of the invention may have pore sizes in a range of about 2.3 Å to about 28.8 Å, and pore volumes that are about 91% of the crystal structure. The MOFs may have a crystal size in a range of about 50 nm to about 1 mm. The MOFs may have a crystalline structure in a variety of shapes such as cubic, spherical, oval, elliptical, fan-shaped, plate-shaped, rectangular, hexagonal, needle, rod, and irregularly shaped. The MOFs may have a surface area in the range of about 100 $m^2/gm$ to about 3000 $m^2/gm$.

The MOFs may be non-isoreticular. Isoreticular MOF's as described in Yaghi, U.S. Pat. No. 6,930,193, have a single net. Non-isoreticular MOFs may have a wider range of adsorption sites to facilitate the adsorption of a wider range of analytes.

Figure 2:
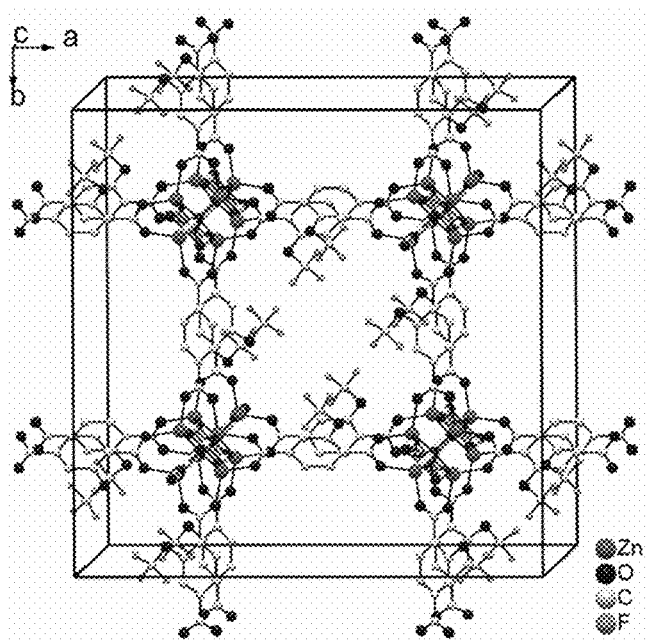
FIG. 2 is a schematic showing the crystal structure of ZnMOF3, according to one principle of the invention.
Figure 2:
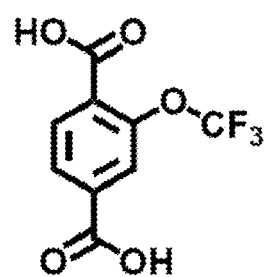

FIG. 2 is a schematic illustrating the MOF, ZnMOF3, according to one embodiment of the invention. In FIG. 2, ZnMOF3 has six bifunctional ligands that coordinate with the edges of $Zn_4O$ core, resulting in an octahedral geometry that confines the framework to a cubic porous network in 3D space. Table 1, below shows the crystal and structure refinement data for ZnMOF3, according to one embodiment of the invention.

TABLE 1

| Compound code | ZnMOF3 |
|---|---|
| Dehydrate Formula | [($Zn_4O$)(2-$CF_3$O-BDC)$_3$] |
| Morphology | Cubic |
| Color | Colorless |
| Temperature | 297(2)K |
| Crystal System | Cubic |
| Space group | Fm-3m |
| a | 25.7650 Å |
| b | 25.7650 Å |
| c | 25.7650 Å |
| α | 90.0° |
| β | 90.0° |
| γ | 90.0° |
| V | 17103.71 Å$^3$ |
| Z | 8 |
| R1 [I > 2sigma(I)] | 0.0990 |
| wR2 | 0.3129 |

Figure 3:
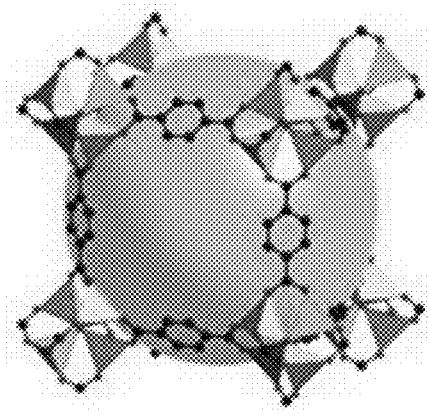
FIG. 3 is a schematic showing the crystal structure of the conventional IRMOF1.

Table 2 below provides a detailed comparison between the conventional, non-water-repellent, cubic-shaped MOF, IRMOF1 reported by Yaghi (Eddaoudi, M.; Kim, J.; Rosi, N.; Vodak, D.; Wachter, J.; O'Keeffe, M.; and Yaghi, O. M., Science 2002, 295, 469-472.) (FIG. 3) and the water-repellent ZnMOF3 of the invention. Since ZnMOF3 has very close unit dimensions to IRMOF1 and its thermal stability and porosity are also comparable to IRMOF1, the performances of each MOF may be compared using the same or similar methods and/or techniques.

TABLE 2

| Name | IRMOF1 | ZnMOF3 |
|---|---|---|
| Crystal system | Cubic | Cubic |
| Space group | Fm-3m | Fm-3m |
| Unit cell dimensions | a = 25.6690(3) Å | a = 25.765(5) Å |
| | α = 90 deg. | α = 90°. |
| | b = 25.6690(3) Å | b = 25.765(5) Å |
| | β = 90 deg. | β = 90°. |
| | c = 25.6690(3) Å | c = 25.765(5) Å |
| | γ = 90 deg. | γ = 90°. |
| Functional ligand | HO-C(=O)-C$_6$H$_4$-C(=O)-OH (terephthalic acid structure) | HO-C(=O)-C$_6$H$_3$(O-CF$_3$)-C(=O)-OH |
| BET measurements | 2700 m$^2$/g | 1700 m$^2$/g |
| Thermal Stability | 420° C. | 350° C. |

The $CF_3O$— functional group in ZnMOF3 is a stable nonpolar functional group, which prevents $H_2O$ molecules from entering the cavities of the MOF frameworks. To verify this point, IRMOF1 and ZnMOF3 were both saturated with water vapor at room temperature. The ZnMOF3 and IRMOF1 samples were prepared for TGA by saturating each sample with toluene, water, DMMP, or nitrobenzene vapors. The saturated sample were analyzed for weight loss using a Mettler-Toledo TGA/SDTA 851e instrument. Specifically, the MOF powders were soaked in $CHCl_3$ for two days to exchange any mother liquor in MOF with $CHCl_3$ framework, the powder collects, and the powder was heated at 150° C. under vacuum to completely remove the $ChCl_3$ solvate. About 5 mg dried sample was then added into a clean test tube. Tested vapor was carried by 15 sccm air flow through a saturator and then passed through the test tube at a temperature in the range of about 20° C. to about 70° C. After 10 µl of solvent loss was observed from the saturator, the saturated samples were collected. TGA analyses were carried out by heating the sample from about 20° C. to about 300° C. at about 15° C./minute.

Figure 4:
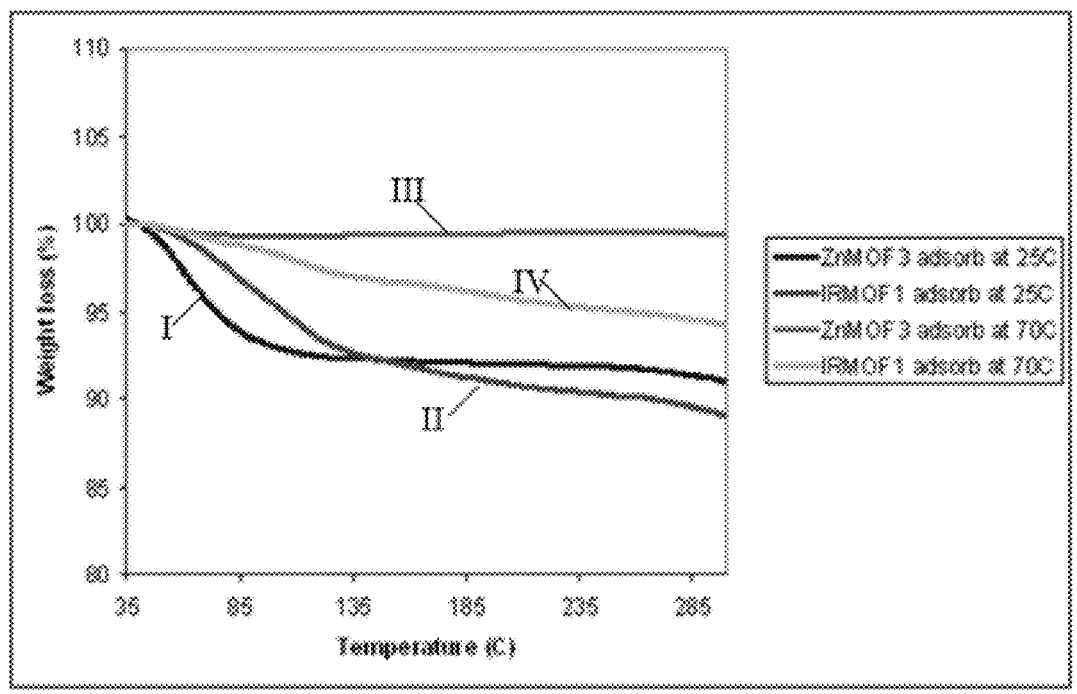
FIG. 4 is am output from TGA analysis of various MOFs comparing the thermal desorption of water from the conventional IRMOF1 with ZnMOF3 prepared according to one principle of the invention, at several temperatures points. The line depicted as I is the thermal desorption of water at 25° C. for ZnMOF3, II is the thermal desorption of water at 25° C. for IRMOF1, III is the thermal desorption of water at 70° C. for ZnMOF3, and IV is the thermal desorption of water at 70° C. for IRMOF1.
Figure 5:
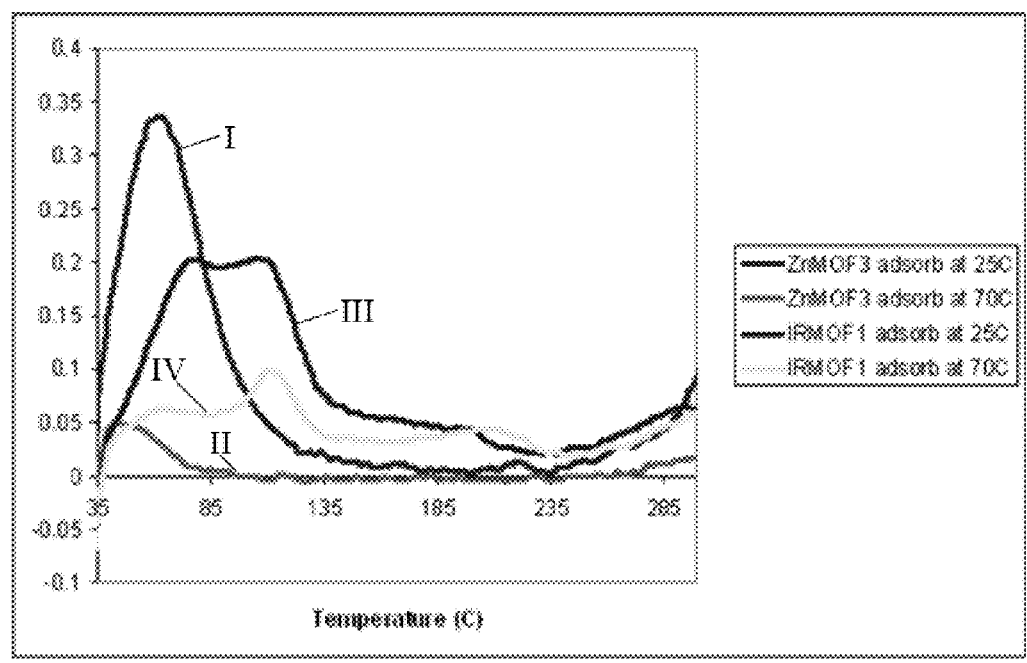
FIG. 5 is a differential scanning calorimetry curve of water desorption TGA curves comparing the conventional IRMOF1 and ZnMOF3, prepared according to one principle of the invention, at several temperature points. The line depicted as I is the differential curve of water desorption for ZnMOF3 at 25° C., II is the differential curve of water desorption for IRMOF1 at 25° C., III is the differential curve of water desorption for ZnMOF3 at 70° C., and IV is the differential curve of water desorption for IRMOF1 at 70° C.

FIG. 4 shows the following TGA measurements: (i) a capacity of 0.11 g $H_2O$/g for IRMOF1, and (ii) a capacity of 0.08 g $H_2O$/g for ZnMOF3. A differential scanning calorimetry study of the two TGA curves revealed that water vapor has three binding sites with IRMOF1 at about 65° C., about 110° C. and about 200° C. respectively, and only one binding site with ZnMOF3 at about 60° C. (FIG. 5). When both MOFs were saturated in water vapors at about 70° C., ZnMOF3 adsorbed nearly no $H_2O$, while IRMOF1 absorbed about 0.05 g $H_2O$/g.

Figure 6:
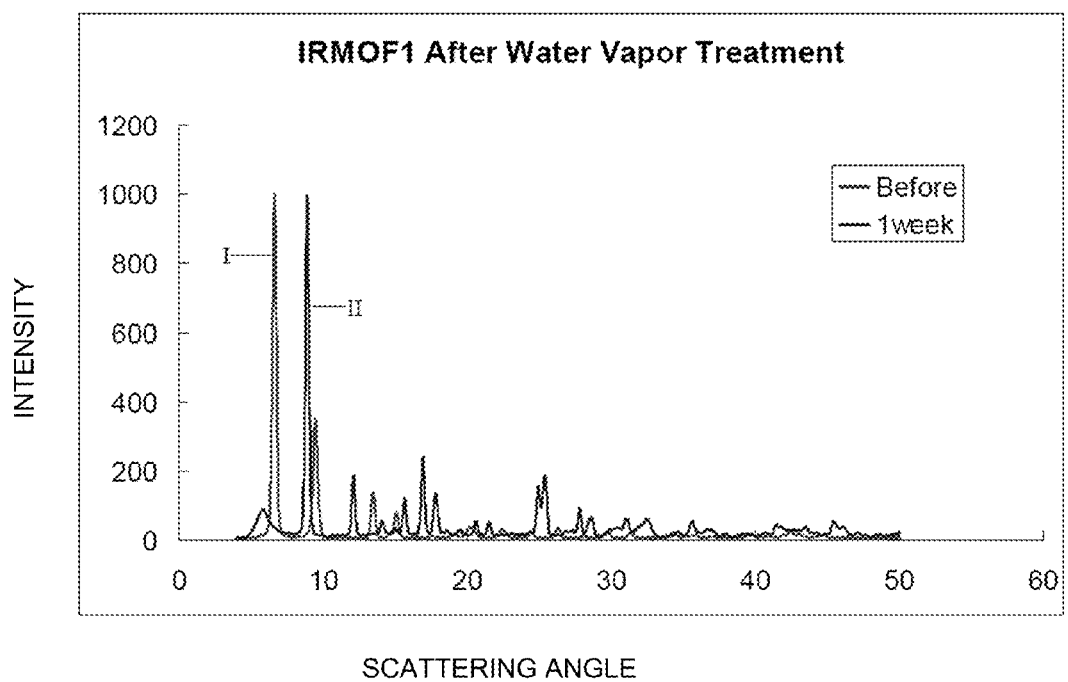
FIG. 6 is an XRPD pattern comparing conventional IRMOF1 before exposure to water vapor treatment (line designated I) and after exposure to water vapor for 1 week (line designated II).
Figure 7:
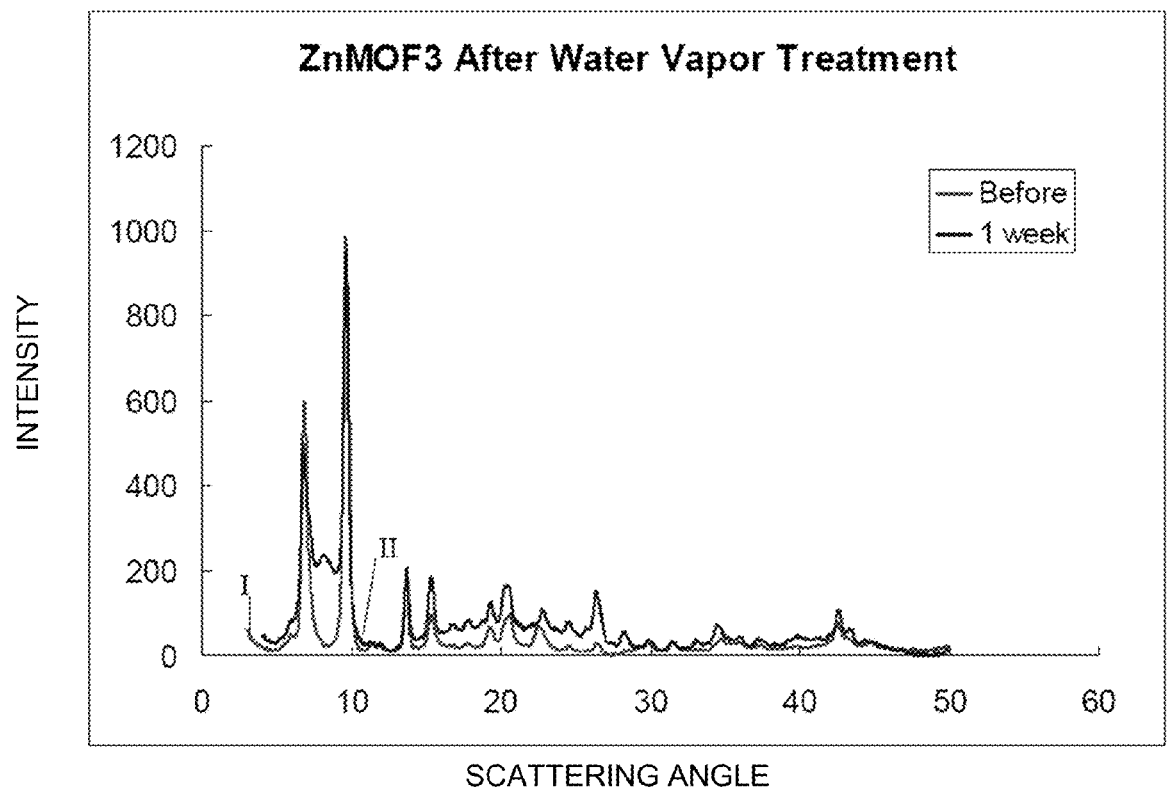
FIG. 7 is an XRPD pattern comparing ZnMOF3, prepared according to one principle of the invention before exposure to water vapor (line designated I) and after exposure to water vapor for 1 week (line designated II).

To further investigate the impact of water on MOF structure, the XRPD spectrum was collected before and after exposing the MOF to boiling water vapor. FIG. 6 shows that after 1 week water exposure, IRMOF1 converted into a different low porous crystal phase. In contrast, as shown in FIG. 7, ZnMOF3 exhibited a high water-repellent behavior, as illustrated by comparing the powder pattern before and after water exposure. A comparison of the major diffraction peaks of ZnMOF3 showed no change before and after exposure to water vapor.

The results shown in FIGS. 4-7 demonstrate that ZnMOF3 has a substantial advantage in applications involving gas-phase absorption. For gas adsorption applications, $H_2O$ always presents as a common interfering substance. Unlike other interfering substances, such as toluene and benzene, water is often present in large concentrations in the air, and it is very polar so it can block adsorption of other molecules. Also, water interferes with the operation of analytical systems, so it must be removed before analysis. In Applicants' application Ser. No. 11/785,102, Applicants have demonstrated that IRMOF1 has an extremely high preconcentration gain for methyl phosphonate vapors. Given ZnMOF3's comparable porosity and thermal stability, ZnMOF3 may be a useful adsorbent having reduces water sorption and may have sorption capacity for many targets of interest.

To verify this point, the sorption capacities of both IRMOF1 and ZnMOF3 were compared using several common targets and interfering substances. As shown in Table 3, below, ZnMOF3 has the same selectivity as IRMOF1 with relatively reduced adsorption capacities.

TABLE 3

| Material | Toluene g adsorbate/ g MOF | DMMP g adsorbate/ g MOF | Nitrobenzene g adsorbate/ g MOF | Water g adsorbate/ g MOF |
|---|---|---|---|---|
| ZnMOF3 | 0.03 | 0.18 | 0.18 | 0.08 |
| IRMOF1 | 0.05 | 0.35 | 0.39 | 0.11 |

In Table 3, above, the reduced sorption capacity of ZnMOF3 is caused by the steric hindrance of the $CF_3O$-groups. Fits of adsorption data indicate that ZnMOF3 repels molecules with strong dipolar polarizability, like water.

A series of common volatile organic compounds (VOCs) breakthrough volume in ZnMOF3 were further measured followed by a similar procedure that was applied on Tenax TA, Tenax GR and carbotraps. Tenax TA and Tenax GR have so far been widely accepted as the most efficient porous adsorbents for trapping of volatiles and semi-volatiles from air.

In order to obtain the breakthrough measurements, about 200 mg of each sample (i.e., IRMOF1 and ZnMOF3) was loaded in the standard Tekmar® thermal desorption tube. The tube was then loaded in the Agilent 5973N GC oven. Helium gas was applied as carrier gas and its flow rate was set at about 40 sccm. The thermal tube was first preconditioned at 200° C. for about 4 hours to about 8 hours until the exhaust signal went down to the bottom line. For liquid phase species, about 2 μL to about 10 μL of corresponding vapor was collected from the head space and was injected at the front entrance of the thermal tube at set temperature; for gaseous phase species, about 2 μL to about 3 μL of corresponding gas was collect from a Teddler bag and was then injected. The exit vapor signal was collected by a FID detector for further analysis.

The breakthrough volume collected in Table 4, below, demonstrate that ZnMOF3 has a much higher breakthrough volumes with most alcohols, and higher or comparable breakthrough volumes for other species as well. This shows that the materials are useful for gas adsorption.

TABLE 4

Breakthrough volumes measured in ZnMOF3 at various temperatures

| | Temperature, ° C. | | | |
|---|---|---|---|---|
| | 0 | 20 | 40 | 60 |
| Acetates | | | | |
| Ethyl Acetate | 650 | 290 | 130 | 60 |
| Hydrocarbons | | | | |
| Methane | 0.028 | 0.015 | 0.008 | 0.005 |
| Ethylene | 0.14 | 0.060 | 0.026 | 0.012 |
| Ethane | 0.15 | 0.092 | 0.055 | 0.033 |
| Propane | 1.28 | 0.65 | 0.326 | 0.17 |
| n-Butane | 12 | 4.90 | 2.00 | 0.82 |
| Pentane | 13 | 7.21 | 3.95 | 2.15 |
| n-Hexane | 38 | 20.5 | 11 | 5.8 |
| n-Decane | 930 | 483 | 251 | 130 |
| Alcohols | | | | |
| Methanol | 72 | 44.3 | 27.4 | 16.9 |
| 2-Methyl-2-Propanol | 1080 | 538 | 268 | 133.8 |
| Ethanol | 188 | 106 | 60.3 | 34.1 |
| 2-Propanol | 490 | 261 | 139 | 74.0 |
| 1-Octanol | 12800 | 5590 | 2450 | 1070 |
| Aldehydes/ketones | | | | |
| Acetaldehyde | 11.82 | 6.08 | 3.12 | 1.60 |
| Acetone | 243.7 | 111.7 | 51.2 | 23.5 |
| Nonanal | 48300 | 19300 | 7740 | 3090 |
| Halogenated compounds | | | | |
| 1,2-Dichloroethylene | 15.9 | 8.85 | 4.94 | 2.75 |
| Trichloroethylene | 21.5 | 11.9 | 6.62 | 3.68 |
| Aromatics | | | | |
| Benzene | 15.1 | 8.876 | 5.235 | 3.09 |
| Toluene | 62.5 | 34.4 | 19.0 | 10.5 |
| Atmospheric Components | | | | |
| Water | 0.276 | 0.198 | 0.142 | 0.102 |
| Others Tested (All had large retention volumes) | | | | |
| Acetic acid, methyl decanoate, dinitrotoluene, di-t-butyl-6-nitro phenol, dodecane, eicosanol, hydroxy-benzaldehyde, isopropylsulfonyl chloride, methoxy-phenyl-oxime, methyl benzaldehyde, methyl decanoate, methyl-2-propanol, dimethylmethylphosphonate | | | | |
| Others Unretained | | | | |
| Hydrogen, Helium, Air | | | | |

According to one embodiment, the MOFs of the invention may be synthesized by a microwave-assisted solvothermal process, as described in U.S. application Ser. No. 11/785,102. According to this process, a reactant solution including MOF ligand is exposed to microwaves for a period of time sufficient to achieve crystallization. The period of time may be, for example, a few seconds to a few minutes or more, depending upon the microwave power and the solution concentration. Time periods may be in a range of about 5 seconds to about 2.5 minut
es.

The MOFs of the invention may also be synthesized by using solvothermal or hydrothermal processes. According to these processes, the solvent used for the reaction solution is dependent upon the organic ligand. Water may be used as the solvent, for example, when the ligand is water soluble. Polar molecule solvents, such as diethyl formamide (DEF) and dimethyl formamide (DMF), for example, are compatible with the mechanism of the microwave assisted synthesis of the invention. Nonpolar solvents, such as benzene are not suitable because they can not be heated in a microwave. This problem can be solved, if necessary, by annealing non-polar solvent with a polar solvent to provide a mixed solvent that can be used in microwave synthesis.

In one embodiment, prior to MOF synthesis, the organic ligand may be pretreated to remove any impurities. For example, metal impurities may be removed by treating the organic ligands with a chelating resin, the $NO_3^-$, $Na^+$, $K^+$ impurities may be removed by subjecting the organic ligands to water soxhlet extraction, the $NO_3^-$, $Na^+$, $K^+$ impurities may be removed by subjecting the organic ligands to liquid-liquid extraction, the $NO_3^-$, $Na^+$, $K^+$ impurities may be removed by subjecting the organic ligands to a bait and switch method, and/or impurities may be removed by subjecting the organic ligands to washing.

In a further embodiment, after the MOFs have been synthesized, the MOFs may be subjected to a post treatment to remove further impurities. For example, the synthesized MOFs may be post-treated by soxhlet extraction to remove impurities using solvents such as ethanol, dichloromethane, benzene, toluene, diethyl ether, chloroform and ethyl acetate. Moreover, the MOFs may be post treated to remove unreacted COOH-groups by treating the MOF with a methylation reagent such as trimethylsulphonium hydroxide (TMSH), N,N-dimethylformamide-dimethylacetal (DMF-DMA), dimethyl carbonate, methyl iodide methanol, ethanol, ethyl iodide, optionally in the presence of an alkaline catalyst such as dimethylimidazole (DMI) or trimethylamine.

The MOFs of the invention may be subjected to pre-treatment purification methods, post-treatment purification, or both. The pre-treatment and post-treatment purifications are further exemplified in specific examples 19-26, below. Table 5, below, show the effects of pretreatment and post treatment on the properties on the ZnMOF3 according to the invention.

TABLE 5

| Sample | Ligand Pretreatment | MOF Posttreatment | Breakthrough volume hexane 100° C. (L/g) | Recovery $(C_2H_5)_3N$ | $C_6H_5CH_2Cl$ % (120° C.) |
|---|---|---|---|---|---|
| 1 | none | none | 3.22 | 0% | 0% |
| 2 | none | 2 hrs $CH_2Cl_2$ Soxhlet | 1.68 | 0% | 96% |
| 3 | none | 2 hrs $CH_3CH_2OH$ Soxhlet | 1.91 | 0% | 96% |
| 4 | none | 7 hrs $CH_3CH_2OH$ Soxhlet | 0.25 | 96% | 91% |
| 5 | none | 7 hrs $CH_3CH_2OH$ Soxhlet + 12 hrs $CH_2Cl_2$ Soxhlet | — | 0% | — |
| 6 | none | 2 hours $CH_3OH$ Soxhlet | MOF Collapsed | | |
| 7 | none | 2 hours pyridine Soxhlet | MOF dissolved | | |
| 8 | methanol/water | none | 11.42 | 0% | 0% |
| 9 | methanol/water | 2 hrs $CH_3CH_2OH$ Soxhlet | 7.06 | 0% | 74% |
| 10 | Water wash | 12 hrs $CH_2CH_2$ soxhlet + dicarbonate | | 90% | |

In another embodiment of the invention, the MOFs may be used as a sorbent of an analyte in a collection system. The collection system may include one of a preconcentrator, micropreconcentrator, personal respirator, and dosimeter. The preconcentrator or micropreconcentrator may be a purge and trap system, microelectromechanical (MEMS) valve system, array of microstructure, dosimeter, disc, pellet, or swab. The MOFs may sorb analytes such as DMMP, PMP, diethyl methylphosphonate (DEMP), diisopropyl methylphosphonate (DIMP), dichlorohexane, malathion, acetic anhydride, TNT, and RDX.

Without further elaboration, it is believed that one skilled in the art using the preceding description can utilize the invention to the fullest extent. The following examples are illustrative only, and not limiting of the disclosure in any way whatsoever.

EXAMPLES

Specific Example 1

Solvothermal Synthesis of ZnMOF3

Zinc nitrate hexahydrate, $Zn(NO_3)_2.6H_2O$, (0.15 g, 0.504 mmol) and 2-trifluoromethoxy terephthalic acid, (2-$CF_3O$—$BDCH_2$) (0.0946 g, 0.378 mmol), were dissolved in about 10 mL diethylformamide. The solution was then sealed in a Pyrex sample vial and heated at about 110° C. Transparent cubic crystals were collected after one week.

Specific Example 2

Microwave Assisted Solvothermal Synthesis of ZnMOF3

Zinc nitrate hexahydrate, $Zn(NO_3)_2.6H_2O$, (0.15 g, 0.504 mmol) and 2-trifluoromethoxy terephthalic acid, (2-trifluoromethoxy-$BDCH_2$) (0.0946 g, 0.378 mmol), were dissolved in about 10 mL diethylformamide. The solution was then sealed in a Pyrex sample vial and heated with a household microwave oven (800 W) for a reaction time of about 80 seconds. The crystals were then soaked in dichloromethane overnight. Next the crystals were dried by heating from room temperature to 170° C. over 5 hours in a clean nitrogen atmosphere, maintained at 170° C. for 3 hours, ramped to 200° C. over 30 minutes, held at 220° C. for 1.4 hours, then cooled to room temperature. The crystals were yellow in cubic shape, with size in a range of about 4 μm to about 7 μm with very few surface defects.

Specific Example 3

Conversion of ZnFOF8 to Non-Isoreticular Form

The MOF in Specific Example 2, above, was placed in a glass thimble. The thimble was placed inside a Wilmad Glass soxhlet extractor equipped with a Friedrichs condenser and round bottom flask loaded with 200 ml EtOH. The MOF was refluxed in EtOH for 2 hours. The resultant MOF was no longer isoreticular, but instead, contained macropores. The macropores may enhance mass transfer of an analyte into the MOF.

Specific Example 3

Microwave Assisted Solvothermal Synthesis of ZnMOF8

Figure 8:
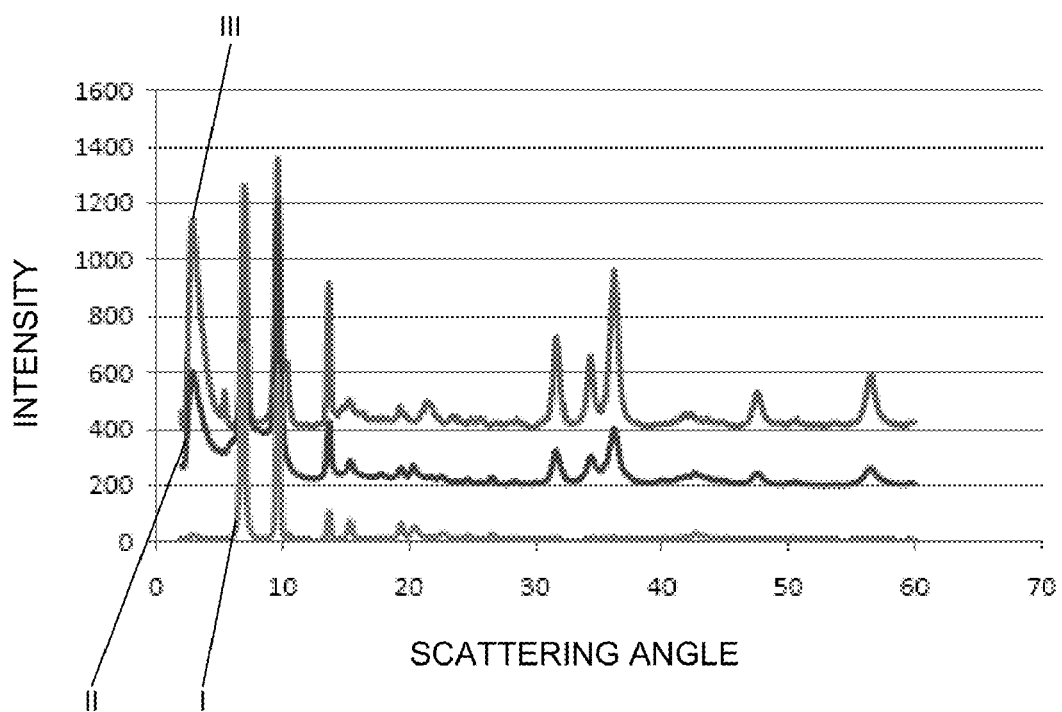
FIG. 8 is an XRPD pattern comparing a MOF synthesized using the dimethyl terephthalic acid ligand obtained from TCI America (Portland, Oreg.) synthesized according to principles of the invention, before exposure to water vapor treatment (line designated I) in comparison to dimethyl-ZnMOF, synthesized by principles of the invention using a dimethyl terephthalic acid ligand synthesized using the procedures of Dyatkina ET AL., J. MEDICINAL CHEMISTRY, 45(4) 805-817 (2002) before exposure to water vapor treatment (line designated II) and after exposure of dimethyl-MOF to water vapor for 2 hours (line designated III).

Zinc nitrate hexahydrate, $Zn(NO_3)_2.6H_2O$, (0.1 g, 0.336 mmol) and 2,5-dimethylterephthalic acid (0.0490 g, 0.252 mmol), were dissolved in about 10 mL diethylformamide. The solution was then sealed in a Pyrex sample vial and heated with a household microwave oven (800 W) for a reaction time of about 30 seconds. The crystals were then soaked in dichloromethane overnight. Next the crystals were dried by heating from room temperature to 170° C. over 5 hours in a clean nitrogen atmosphere, maintained at 170° C. for 3 hours, ramped to 200° C. over 30 minutes, held at 220° C. for 1.4 hours, then cooled to room temperature. The resulting crystals have a cubic shape and a light yellow color, having a size in a range of about 1 μm to about 3 μm. FIG. 8 is a XPDP pattern showing the water stability of ZnMOF8 before and after exposure to water vapor for 2 hours. The XPDP shows that ZnMOF8 is water repellent.

Specific Example 4

Microwave Assisted Solvothermal Synthesis of CuMOF5

Cupric nitrate, $Cu(NO_3)_2.xH_2O$, (0.1 g, 0.533 mmol) and 2,5-dimethylterephthalic acid, (0.0776 g, 0.400 mmol), were dissolved in about 10 mL diethylformamide. The solution was then sealed in a Pyrex sample vial and heated with a household microwave oven (800 W) for a reaction time of about 30 seconds. The crystals were then soaked in dichloromethane overnight. Next the crystals were dried by heating from room temperature to 170° C. over 5 hours in a clean nitrogen atmosphere, maintained at 170° C. for 3 hours, ramped to 200° C. over 30 minutes, held at 220° C. for 1.4 hours, then cooled to room temperature. The resultant crystals were irregularly shaped.

Specific Example 5

Microwave Assisted Solvothermal Synthesis of CuMOF6

Cupric nitrate, $Cu(NO_3)_2.xH_2O$, (0.1 g, 0.533 mmol) and 2,5-dimethoxyterephthalic acid, (0.090 g, 0.400 mmol), were dissolved in about 10 mL diethylformamide. The solution was then sealed in a Pyrex sample vial and heated with a household microwave oven (800 W) for a reaction time of about 30 seconds. The crystals were then soaked in dichloromethane overnight. Next the crystals were dried by heating from room temperature to 170° C. over 5 hours in a clean nitrogen atmosphere, maintained at 170° C. for 3 hours, ramped to 200° C. over 30 minutes, held at 220° C. for 1.4 hours, then cooled to room temperature. The resultant crystals were fan-shaped.

Specific Example 6

Microwave Assisted Solvothermal Synthesis of CdMOF4

Cadmium nitrate tetrahydrate, $Cd(NO_3)_2.4H_2O$, (0.1 g 0.324 mmol) and 2,5-dimethoxyterephthalic acid, (0.055 g, 0.243 mmol), were dissolved in 10 mL diethylformamide. The solution was then sealed in a Pyrex sample vial and heated with a household microwave oven (800 W) for a reaction time of about 30 seconds. The crystals were then soaked in dichloromethane overnight. Next the crystals were dried by heating from room temperature to 170° C. over 5 hours in a clean nitrogen atmosphere, maintained at 170° C. for 3 hours, ramped to 200° C. over 30 minutes, held at 220° C. for 1.4 hours, then cooled to room temperature. The resultant crystals were plate-shaped.

Specific Example 7

Microwave Assisted Solvothermal Synthesis of ZnMOF9

Zinc nitrate hexahydrate, $Zn(NO_3)_2.6H_2O$, (0.1 g, 0.336 mmol) and 2,5-dimethoxyterephthalic acid (0.0570 g, 0.252 mmol), were dissolved in about 10 mL diethylformamide. While the mixture was stirred, 6 μl of triethylamine and 1 mg NaOH were added. The solution was stirred for another 15 minutes and then sealed in a Pyrex sample vial and heated with a household microwave oven (800 W) for a reaction time of about 30 seconds. The crystals were then soaked in dichloromethane overnight. Next the crystals were dried by heating from room temperature to 170° C. over 5 hours in a clean nitrogen atmosphere, maintained at 170° C. for 3 hours, ramped to 200° C. over 30 minutes, held at 220° C. for 1.4 hours, then cooled to room temperature. The resultant crystals have cubic shape in light yellow color, having a size in a range of about 4 μm to about 8 μm.

Specific Example 8

Microwave Assisted Solvothermal Synthesis of CuMOF2

Exact amount of cupric nitrate, $Cu(NO_3)_2.2.5H_2O$, (0.1 g, 0.430 mmol) and 2-(trifluoromethoxy) terephthalic acid (0.0807 g, 0.322 mmol), were dissolved in 10 mL diethylformamide. The solution was then sealed in a Pyrex sample vial and heated with a household microwave oven (800 W) for a reaction time 80 seconds. The crystals were then soaked in dichloromethane overnight. Next the crystals were dried by heating from room temperature to 170° C. over 5 hours in a clean nitrogen atmosphere, maintained at 170° C. for 3 hours, ramped to 200° C. over 30 minutes, held at 220° C. for 1.4 hours, then cooled to room temperature.

Specific Example 9

Microwave Assisted Solvothermal Synthesis of ZnMOF7

Zinc nitrate hexahydrate, $Zn(NO_3)_2*6H_2O$, (0.15 g, 0.504 mmol) and 2,5-furandicarboxylic acid (0.059 g, 0.378 mmol), were dissolved in 10 mL diethylformamide. The solution was then sealed in a Pyrex sample vial and heated with a household microwave oven (800 W) for a reaction time of about 50 seconds. The resultant crystals were tetrahedron shape and are not stable when exposed to water.

Specific Example 10

Microwave Assisted Solvothermal Synthesis of ZnMOF10

Zinc nitrate hexahydrate, $Zn(NO_3)_2.6H_2O$, (0.1 g, 0.336 mmol) and 2,5-dichloroterephthalic acid, (0.059 g, 0.252 mmol), were dissolved in 10 mL diethylformamide. The solution was then sealed in a Pyrex sample vial and heated with a household microwave oven (800 W) for a reaction time of about 40 seconds. The resulting crystals have irregular shape with yellow color and are not stable when exposed to water.

Specific Example 11

Microwave Assisted Solvothermal Synthesis of ZnMOF11

Zinc nitrate hexahydrate, $Zn(NO_3)_2.6H_2O$, (0.1 g, 0.336 mmol) and 2-methylterephthalic acid (0.0454 g, 0.252 mmol), were dissolved in 5 mL diethylformamide. The solution was then sealed in a Pyrex sample vial and heated with a household microwave oven (800 W) for a reaction time of 30 seconds. The resultant crystals were yellow color having a cubic shape, with size in a range of about 2 μm to about 4 μm.

Specific Example 12

Microwave Assisted Solvothermal Synthesis of ZnMOF12

Zinc nitrate hexahydrate, $Zn(NO_3)_2.6H_2O$, (0.1 g, 0.336 mmol) and 2,5-diethylterephthalic acid (0.056 g, 0.252 mmol), were dissolved in 5 mL diethylformamide. The solution was then sealed in a Pyrex sample vial and heated with a household microwave oven (800 W) for a reaction time of 25 seconds. The resultant crystals were light yellow having a cubic shape, with size in a range of about 2 μm to about 4 μm.

Specific Example 13

Microwave Assisted Solvothermal Synthesis of ZnMOF13

Zinc nitrate hexahydrate, $Zn(NO_3)_2.6H_2O$, (0.1 g, 0.336 mmol) and 2-methoxyterephthalic acid (0.049 g, 0.252 mmol), were dissolved in 5 mL diethylformamide. The solution was then sealed in a Pyrex sample vial and heated with a household microwave oven (800 W) for a reaction time of 30 seconds. The resultant crystals were light yellow having a cubic shape, with size in a range of about 1 µm to about 7 µm.

Specific Example 14

Microwave Assisted Solvothermal Synthesis of CuMOF4

Cupric nitrate, $Cu(NO_3)_2 \cdot xH_2O$, (0.1 g, 0.533 mmol) and 2-bromoterephthalic acid, (0.098 g, 0.400 mmol), were dissolved in about 10 mL diethylformamide. The solution was then sealed in a Pyrex sample vial and heated with a household microwave oven (800 W) for a reaction time of about 30 seconds. The resultant crystals were plate with square shape and green color and were not stable when exposed to water.

Specific Example 15

Microwave Assisted Solvothermal Synthesis of CuMOF7

Cupric nitrate, $Cu(NO_3)_2 \cdot xH_2O$, (0.1 g, 0.533 mmol) and 2,5-dichloroterephthalic acid, (0.094 g, 0.400 mmol), were dissolved in about 10 mL diethylformamide. The solution was then sealed in a Pyrex sample vial and heated with a household microwave oven (800 W) for a reaction time of about 40 seconds. The resultant crystals were plate with square shape and green color and were not stable when exposed to water.

Specific Example 16

Microwave Assisted Solvothermal Synthesis of CuMOF8

Cupric nitrate, $Cu(NO_3)_2 \cdot xH_2O$, (0.1 g, 0.533 mmol) and 2,5-diethoxyterephthalic acid, (0.089 g, 0.400 mmol), were dissolved in about 5 mL diethylformamide. The solution was then sealed in a Pyrex sample vial and heated with a household microwave oven (800 W) for a reaction time of about 35 seconds. The resultant crystals had a petal like shape with dark green color.

Specific Example 17

Microwave Assisted Solvothermal Synthesis of CuMOF9

Cupric nitrate, $Cu(NO_3)_2 \cdot xH_2O$, (0.1 g, 0.533 mmol) and 2-methoxyterephthalic acid, (0.078 g, 0.400 mmol), were dissolved in about 5 mL diethylformamide. The solution was then sealed in a Pyrex sample vial and heated with a household microwave oven (800 W) for a reaction time of about 30 seconds. The resultant crystals were square plate shape with dark green color.

Specific Example 18

Microwave Assisted Solvothermal Synthesis of GdMOF1

$Gd(NO_3)_3 \cdot 6H_2O$, (0.15 g, 0.332 mmol) and terephthalic acid, (0.021 g, 0.249 mmol), were dissolved in 10 mL diethylformamide. The solution was then sealed in a Pyrex sample vial and heated with a household microwave oven (800 W) for a reaction time of about 30 seconds. The resultant yellow crystals were parallelogram shape with size in the range of about 0.5 µm to about 2 um.

Specific Example 19

Purification Treatment of Organic Ligands by Using a Chelating Resin to Remove Transition Metal Impurities The following chelating resins can be applied for this purpose: Amberlite IRC748I, Dowex M4195, Lewatit TP-208 and Chelex 100.

20-30 gram chelating resin was mixed with 100 ml MeOH. The resulting slurry was then packed in a glass column with frit at the bottom. If the resin was in the form of its sodium salt, it was first conditioned using 1M aqueous HCl or $H_2SO_4$. Subsequently, the column was rinsed 3-5 times with fresh MeOH.

1 g of 2-trifluoromethoxy terephthalic acid was dissolved in 50 ml of MeOH, and the resulting solution was added to the top of the column. The eluent was collected in a 100 ml beaker and then was used to re-feed the column. After the eluent was passed through the column three times, 40 ml of fresh MeOH was added to remove any remaining ligand from the column. The ligand was collected by removing the solvent under reduced pressure using rotary evaporator and the resulting material dried at 110° C. for 2 hours.

Specific Example 20

Purification Treatment of Organic Ligands by Removing $NO_3^-$, $Na^+$, $K^+$ Impurities by Soxhlet Extraction Using Water 1 gram of 2-trifluoromethoxy terephthalic acid was added into a glass thimble, and the thimble placed inside a soxhlet extractor. Refluxing millipore grade water was used to extract impurities from the acid for about 12 hours. The final product was dried at 110° C. for 2 hours.

Specific Example 21

Purification Treatment of Organic Ligands by Removing $NO_3^-$, $Na^+$, $K^+$ Impurities by Liquid-Liquid Extraction 2.26 gram of 2-trifluoromethoxyterephthalic acid was dissolved in 125 ml ethyl acetate. The resulting solution was filtered through paper to remove un-dissolved impurities. Water soluble impurities were extracted by washing the paper filter 3 times with 20 ml millipore grade water. The ligand in the organic phase was then collected by rotary evaporation and dried at 110° C. for 2 hours.

Specific Example 22

Purification Treatment of Organic Ligands by Removing $NO_3^-$, $Na^+$, $K^+$ Impurities by Evaporation and Precipitation 2.12 g of 2-trifluoromethoxyterephthalic acid and 50 ml MeOH was added into a 200 ml flask. 60 ml of millipore grade water was then added to the flask. The flask was placed in a 50° C. water bath for 1 hour to evaporate most of the MeOH from the mixture. The yellow precipitate was collected by vacuum filtration. The ligand was further dried at 110° C. for 2 hours.

Example 23

Purification Treatment of Organic Ligands by Removing Metals By Washing 3 ml of HPLC grade 50% formic acid (Sigma) was added to 3 liters of 100 megaohm-cm water in a 5 L flask. 322 grams of 2-methylterephthalic acid was added to the mixture and the mixture stirred for about 2 hours to about 12 hours. The ligand was collected by filtration and dried at 110° C. for 2 hours.

Specific Example 24

Post-Treatment Following MOF Synthesis by Soxhlet Extraction to Remove Impurities 10 gram of a MOF was placed in a glass thimble. The thimble was placed inside a soxhlet extractor equipped with a Friedrichs condenser and round bottom flask loaded with 200 ml EtOH. The mixture was refluxed using either EtOH or dichloromethane for about 2 hours to about 12 hours. The final product was dried at ambient temperature.

Specific Example 25

Post-Treatment Following MOF Synthesis by Conditioning MOF using $CH_2Cl_2$ Soxhlet Extraction 10 g of a MOF were placed in a glass thimble. The thimble was placed inside a soxhlet extractor equipped with a Friedrichs condenser and a round bottom flask loaded with 200 ml $CH_2Cl_2$. The impurities were extracted by reflux $CH_2Cl_2$ and residual DEF/DMF mother solvent (from making the MOF) for at least 2 hours. The final product was dried at ambient temperature. The product was baked from room temperature to 120° C. at 0.5° C./min under a $N_2$ atmosphere flow or under vacuum, and then further conditioned at 120° C. for another 30 min. The product was finally cooled.

Specific Example 26

Post-Treatment following MOF Synthesis by Removing Unreacted COOH— Groups

Methylterephthalic acid was washed as in specific example 23, above, and then converted to ZnMOF11 as indicated in specific example 11, above. The MOF was then treated as described in specific example 25, above. 146 milligrams of the resultant powder, 42.7 mg of dimethylimidazole (DMI), 5 milliliters of dimethylformamine (DMF), and 1 ml of dimethylcarbonate (DMC) was loaded into a 10 ml pressurized sealed vial. The mixture was heated to 120° C. in a CEM microwave for 12 minutes. The product was baked from room temperature to 120° C. at 0.5° C./min under a $N_2$ atmosphere flow or under vacuum, and then further conditioned at 120° C. for another 30 min. The final product was cooled.

Specific Example 27

Microwave Synthesis of Larger MOF Particles

Zinc nitrate hexahydrate, $Zn(NO_3)_2 \cdot 6H_2O$, (4.8 g, 0.016 mol) and 2-methylterephthalic acid, (2.18 g, 0.012 mol), were dissolved in 120 ml dimethylformamide. The solution was then sealed in MARS reaction tubes (CEM Corp) with 20 ml solvent in each tube. The 6 tubes were then heated in a MARS microwave (CEM) until the solvent temperature reached 180° C. The resultant crystals had a wide size distribution with most of the particles in the range of about 0.5 µm to about 20

Specific Example 28

Microwave Synthesis of Larger IRMOF1

Zinc nitrate hexahydrate, $Zn(NO_3)_2 \cdot 6H_2O$, (20 g, 0.07 mol) and terephthalic acid, (8.38 g, 0.05 mol), were dissolved in 2000 ml dimethylformamide. The solution was sealed in 40 Multiple Automated Reactor System (MARS) reaction tubes with 50 ml of solvent in each tube. The 40 tubes were then heated in a MARS for about 30 minutes or until the solvent temperature reached 150° C. The resultant crystals had a wide size distribution with most of the particles between about 5 µm to about 40 µm.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

What is claimed is:
1. A metal organic framework (MOF), comprising:
a plurality of metals and/or metal oxides and a plurality of ligands arranged to form a crystalline structure having a surface area of at least about 100 $m^2/gm$, wherein said plurality of ligands have a structure of formula I;

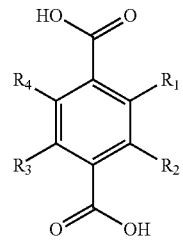

Formula 1 wherein $R_1$ is $DY_3$ or $A-DY_3$ or $A-B-DY_3$,
wherein $R_2-R_4$ is $DY_3$ or $A-DY_3$ or $A-B-DY_3$ or hydrogen;
wherein A is O or S and B is $DY_2$ or O or S,
each D is independently C or Si,
each Y is independently hydrogen, fluorine, chlorine, or bromine,
with the provisos that (i) at least one of A or B must be $DY_2$ in $A-B-DY_3$ and (ii) when D in $DY_2$ is Si, Y is hydrogen, chlorine, or fluorine.

2. The MOF of claim 1, wherein the major peaks in the X-ray powder diffraction (XRPD) spectrum of said MOF do not significantly shift when the MOF is exposed to water vapor for greater than about 1 hour, wherein the XPDP of the MOF before and after exposure to water vapor is substantially unchanged.

3. The MOF of claim 1, wherein said metal is one or more metals selected from the group consisting of magnesium, cadmium, beryllium, copper, terbium, gadolinium, iron, nickel, cobalt, silver and zinc.

4. The MOF of claim 1, wherein said metal oxide is one or more metal oxides selected from the group consisting of magnesium oxide, cadmium oxide, beryllium oxide, copper oxide, terbium oxide, gadolinium oxide, iron oxide, nickel oxide, cobalt oxide, silver oxide and zinc oxide.

5. The MOF of claim 1, wherein said metal is zinc and wherein $R_1$ is a methyl, ethyl, methoxy, trifluoromethyl, 1,1,1-trifluoroethyl, or trifluoromethoxy group and at least one of $R_2$, $R_3$, and $R_4$ is hydrogen.

6. The MOF of claim 1, wherein said metal is zinc and wherein at least one of $R_1$ and $R_3$ is a methyl, ethyl, methoxy, trifluoromethyl, 1,1,1-trifluoroethyl, or trifluoromethoxy group and at least one of $R_2$ and $R_4$ is hydrogen.

7. The MOF of claim 1, wherein said metal is copper and wherein at least one of $R_1$ and $R_3$ is a ethyl or methyl group and at least one of $R_2$ and $R_4$ is hydrogen.

8. The MOF of claim 1, wherein said metal is copper and wherein at least one of $R_1$ and $R_3$ is a methoxy group and at least one of $R_2$ and $R_4$ is hydrogen.

9. The MOF of claim 1, wherein said metal is cadmium and wherein at least one of $R_1$ and $R_3$ is a methoxy group and at least one of $R_2$ and $R_4$ is hydrogen.

10. The MOF of claim 1, wherein said crystalline structure is a non-linear structure.

11. The MOF of claim 10, wherein the non-linear structure is selected from the group consisting of cubic, spherical, oval, elliptical, fan-shaped, plate-shaped, rectangular, hexagonal, needle, rod, and irregularly shaped.

12. The MOF of claim 1, wherein said MOF is non-isoreticular.

13. The MOF of claim 1, wherein at least one of $R_1$ and $R_2$, and at least one of $R_3$ and $R_4$ are non-polar functional groups.

14. The MOF of claim 1, wherein said crystalline structure has a plurality of micropores.

15. The MOF of claim 14, wherein the pores have a size in a range of about 1 nm to about 3 nm.

16. The MOF of claim 1, wherein the MOF contains a plurality of macropores.

17. The MOF of claim 1, wherein the MOF includes a plurality of particles having a diameter less than about 40 nm.

18. A collection system comprising a sorbent for an analyte, wherein the sorbent is the MOF of claim 1.

19. The MOF of claim 18, wherein the collection system comprises one of a preconcentrator, micropreconcentrator, personal respriator, and dosimeter.

20. The MOF of claim 19, wherein one of the preceoncentrator or micropreconcentrator is a purge and trap system, microelectromechanical (MEMS) valve system, array of microstructures, dosimeter, disc, pellet, or swab.

* * * * *